US012759980B2

(12) United States Patent
Moussa et al.

(10) Patent No.: US 12,759,980 B2

(45) Date of Patent: Oct. 13, 2026

(54) NEURODEGENERATIVE, MYODEGENERATIVE, AND LYSOSOMAL STORAGE DISORDERS

(71) Applicant: GEORGETOWN UNIVERSITY, Washington, DC (US)

(72) Inventors: Charbel Moussa, Washington, DC (US); Christian Wolf, Washington, DC (US); Balaraman Kaluvu, Washington, DC (US)

(73) Assignee: GEORGETOWN UNIVERSITY, Washington, DC (US)

( * ) Notice: Subject to any disclaimer, the term of this patent is extended or adjusted under 35 U.S.C. 154(b) by 1027 days.

(21) Appl. No.: 17/759,806

(22) PCT Filed: Jan. 29, 2021

(86) PCT No.: PCT/US2021/015772

§ 371 (c)(1),
(2) Date: Jul. 29, 2022

(87) PCT Pub. No.: WO2021/155195

PCT Pub. Date: Aug. 5, 2021

(65) Prior Publication Data

US 2023/0095341 A1 Mar. 30, 2023

Related U.S. Application Data

(60) Provisional application No. 62/967,345, filed on Jan. 29, 2020.

(51) Int. Cl.

| | |
|---|---|
| ***C07D 215/44*** | (2006.01) |
| ***A61K 45/06*** | (2006.01) |
| ***A61P 25/00*** | (2006.01) |
| ***C07C 229/60*** | (2006.01) |
| ***C07D 215/233*** | (2006.01) |
| ***C07D 217/22*** | (2006.01) |

(52) U.S. Cl.

CPC ............ *C07D 215/44* (2013.01); *A61K 45/06* (2013.01); *A61P 25/00* (2018.01); *C07C 229/60* (2013.01); *C07D 215/233* (2013.01); *C07D 217/22* (2013.01)

(58) Field of Classification Search

CPC ......................... C07D 214/44; C07D 214/233; C07D 217/22; A61P 25/00; A61K 45/06; C07C 229/60

See application file for complete search history.

(56) References Cited

U.S. PATENT DOCUMENTS

| | | | |
|---|---|---|---|
| 5,145,843 | A | 9/1992 | Arnold et al. |
| 5,245,036 | A | 9/1993 | Robey et al. |
| 6,093,732 | A | 7/2000 | Tucker et al. |
| 6,479,511 | B1 | 11/2002 | Knauf-beiter et al. |
| 6,552,039 | B2 | 4/2003 | Knauf-beiter et al. |
| 2015/0284405 | A1 | 10/2015 | Trzupek et al. |

FOREIGN PATENT DOCUMENTS

| | | | | |
|---|---|---|---|---|
| EP | 0393926 | A1 | | 10/1990 |
| EP | 0422328 | A2 | | 4/1991 |
| JP | 43020294 | | * | 8/1968 |
| WO | 2007071055 | A1 | | 6/2007 |
| WO | 2008020081 | A1 | | 2/2008 |
| WO | 2008091555 | A2 | | 7/2008 |
| WO | 2009114729 | A2 | | 9/2009 |
| WO | 2010030967 | A1 | | 3/2010 |
| WO | 2019173482 | A1 | | 9/2019 |

OTHER PUBLICATIONS

Otevrel et al., 18(9) Molecule 10648-10670 (2013) (Year: 2013).*

Niementowski, St. V., 40 Berichte der Deutschen Chemischen Gesellschaft 4285-94 (1908) (CAS Abstract) (Year: 1908).*

International Application No. PCT/US2021/015772 , "International Preliminary Report on Patentability", Aug. 11, 2022, 8 pages.

International Application No. PCT/US2021/015772 , "International Search Report and Written Opinion", Jun. 3, 2021, 11 pages.

International Application No. PCT/US2021/015772 , "Invitation to Pay Additional Fees and, Where Applicable, Protest Fee", Mar. 24, 2021, 3 pages.

CA3,166,527 , "Office Action", Sep. 12, 2023, 4 pages.

EP21748092.0, "Partial Supplementary European Search Report", Dec. 11, 2023, 15 pages.

Hollerhage et al., "Natural Lipophilic Inhibitors of Mitochondrial Complex I Are Candidate Toxins for Sporadic Neurodegenerative Tau Pathologies", Experimental Neurology, vol. 220, No. 1, Nov. 1, 2009, pp. 133-142.

CA3166527, "Office Action", May 1, 2024, 4 pages.

Cope et al., "Synthesis and SAR study of acridine, 2-methylquinoline and 2-phenylquinazoline analogues as anti-prion agents", European Journal of Medicinal Chemistry, vol. 41, No. 10, Oct. 1, 2006, pp. 1124-1143.

EP21748092.0, "Extended European Search Report", Apr. 18, 2024, 21 pages.

Szabadkai et al., "Discovery of N-[4-(Quinolin-4-yloxy)phenyl]benzenesulfonamides as Novel AXL Kinase Inhibitors", Journal of Medicinal Chemistry vol. 61, No. 14, Jun. 21, 2018, pp. 6277-6292.

Canadian Application No. 3,166,527, Notice of Allowance, Mailed on Dec. 19, 2025, 1 page.

* cited by examiner

*Primary Examiner* — Timothy R Rozof

(74) *Attorney, Agent, or Firm* — Kilpatrick Townsend & Stockton LLP

(57) ABSTRACT

Provided herein are compositions and methods for treating or preventing a neurodegenerative disease, a neurodevelopmental disease, a myodegenerative disease, a prion disease, a lysosomal storage disease or cancer in a subject.

11 Claims, 17 Drawing Sheets

Fig. 3A
Fig. 3B
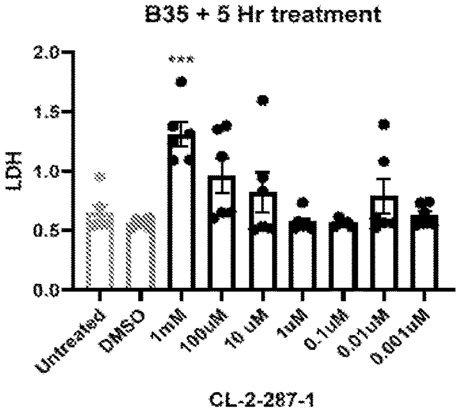
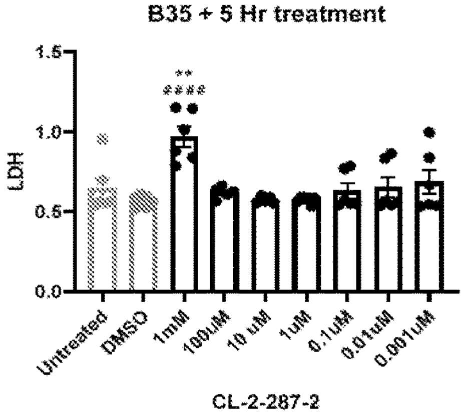
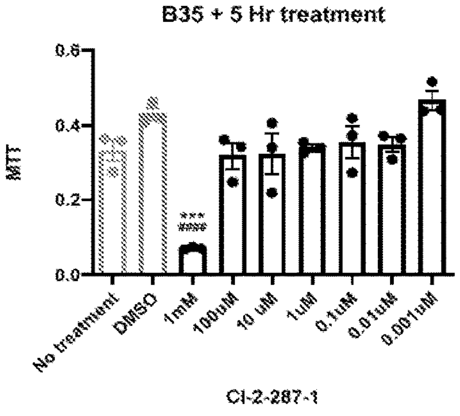
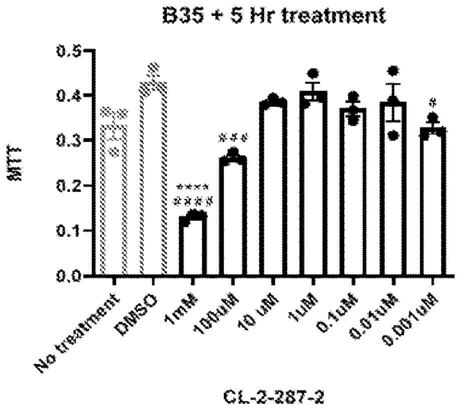

NEURODEGENERATIVE, MYODEGENERATIVE, AND LYSOSOMAL STORAGE DISORDERS

CROSS-REFERENCE TO PRIORITY APPLICATION

This application claims priority to U.S. Provisional Application No. 62/967,345, filed Jan. 29, 2020, which is hereby incorporated in its entirety by this reference.

BACKGROUND

Neurodegenerative diseases include genetic and sporadic disorders associated with progressive nervous system dysfunction. These diseases are characterized by progressive deterioration of nerve cells or nerve cell function. It has been estimated that one of four Americans will develop a neurodegenerative condition in their lifetimes. Generally, however, the underlying mechanisms causing the conditions are not well understood and few effective treatment options are available for preventing or treating neurodegenerative diseases.

Neurodevelopmental disorders for example, autism spectrum disorder (ASD) or attention deficit hyperactivity disorder (ADHD), often affect a person's emotions, learning ability, self-control and memory. These effects often persist over a person's lifespan. According to the Centers for Disease Control, about 1 in 54 children has been identified with ASD, with the disorder being four times more common among boys than among girls. Despite the prevalence of neurodevelopmental disorders, for example, ASD, effective treatment options are limited.

Lysosomal storage disorders represent some of the most devastating of genetic diseases, and the need to develop therapies for these disorders remains largely unmet. Many of these diseases cause damage to the central nervous system (CNS), but the mechanisms underlying such damage are largely unknown. Although the incidence of lysosomal storage disorders is rare (less than about 1:100,000 individuals is affected, lysosomal storage disorders affect mostly children who often die at a young age, many within a few months or years of birth. Many other children die following years of suffering from various symptoms of their particular lysosomal storage disorder.

SUMMARY

Provided herein are compositions and methods for treating or preventing a neurodegenerative disease, a neurodevelopmental disorder, a myodegenerative disease, a prion disease or a lysosomal storage disease in a subject. Provided herein are compounds having Formula I:

Formula I

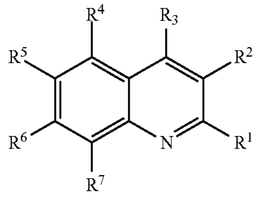

wherein $R^1$ is $NR^8R^9$, $CR^8R^9R^{10}$, or $OR^8$, wherein $R^8$, $R^9$, and $R^{10}$ are each independently H, OH, substituted or unsubstituted aryl (e.g., substituted or unsubstituted phenyl), substituted or unsubstituted alkyl, cycloalkyl, heteroalkyl, cycloheteroalkyl, or heteroaryl;

$R^2$, $R^4$, $R^5$, $R^6$ and $R^7$ are each independently H, OH, halogen, $C_{1-6}$ alkyl, or $C_{1-6}$ alkoxy; and $R^3$ is $NR^{11}R^{12}$ or $OR^{11}$, wherein $R^{11}$ and $R^{12}$ are each independently H, OH, substituted or unsubstituted aryl (e.g., substituted or unsubstituted phenyl), substituted or unsubstituted alkyl, cycloalkyl, heteroalkyl, cycloheteroalkyl, or heteroaryl.

Also provided are compounds having Formula II:

Formula II

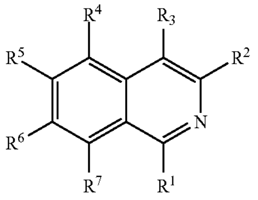

wherein $R^1$ is $NR^8R^9$, $CR^8R^9R^{10}$, or $OR^8$, wherein $R^8$, $R^9$ and $R^{10}$ are each independently H or substituted or unsubstituted aryl (e.g., substituted or unsubstituted phenyl);

$R^2$, $R^3$, $R^4$, $R^6$, and $R^7$ are each independently H, OH, $C_{1-6}$ alkyl, or $C_{1-6}$ alkoxy; and $R^5$ is $NR^{11}R^{12}$ or $OR^{10}$, wherein $R^{11}$ and $R^{12}$ are each independently H, OH, substituted or unsubstituted alkyl, cycloalkyl, heteroalkyl, cycloheteroalkyl, or heteroaryl.

Further provided are compounds having Formula III:

Formula III

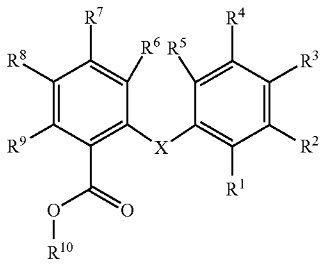

wherein

X is $NR^{11}$, S, or O;

$R^{11}$ is H, substituted or unsubstituted alkyl, or substituted or unsubstituted aryl; or substituted or unsubstituted cycloalkyl, heteroalkyl, cycloheteroalkyl, or heteroaryl;

$R^1$ is H or $C_1$-$C_6$ alkyl;

$R^2$ is H, OH, halogen (e.g., F, Cl, Br, or I), or $C_1$-$C_6$ alkyl;

$R^3$, $R^4$, $R^5$, $R^6$, $R^7$, $R^8$, and $R^9$ are each independently H, OH, $C_{1-6}$alkyl, or $C_{1-6}$alkoxy; and $R^{10}$ is H or $C_{1-6}$ alkyl.

Also provided is a method of treating or preventing a neurodegenerative disease, a neurodevelopmental disorder, a myodegenerative disease, a prion disease or a lysosomal storage disorder (LSD) in a subject, comprising administering to the subject with the neurodegenerative disease, a neurodevelopmental disorder, the myodegenerative disease, the prion disease or the LSD or at risk for developing the neurodegenerative disease, a neurodevelopmental disorder, the myodegenerative disease the prion disease or the LSD, an effective amount of a compound having Formula I:

Formula I

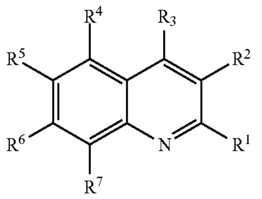

wherein $R^1$ is H, $NR^8R^9$, $CR^8R^9$, or $OR^8$, wherein $R^8$ and $R^9$ are each independently H, OH, substituted or unsubstituted aryl(e.g., substituted or unsubstituted phenyl), or substituted or unsubstituted alkyl;

$R^2$, $R^4$, $R^5$, $R^6$, and $R^7$ are each independently H, OH, halogen, $C_{1-6}$alkyl, or $C_{1-6}$ alkoxy. In some examples, $R^6$ is halogen (e.g., F, Cl, Br, or I); and $R^3$ is $NR^{11}R^{11}$ or $OR^{10}$, wherein $R^{10}$ and $R^{11}$ are each independently H, OH, substituted or unsubstituted aryl (e.g., substituted or unsubstituted phenyl), or substituted or unsubstituted alkyl.

Also provided is a method of treating or preventing a neurodegenerative disease, a neurodevelopmental disorder, a myodegenerative disease, a prion disease or a lysosomal storage disorder (LSD) in a subject, comprising administering to the subject with the neurodegenerative disease, a neurodevelopmental disorder, the myodegenerative disease, the prion disease or the LSD or at risk for developing the neurodegenerative disease, a neurodevelopmental disorder, the myodegenerative disease the prion disease or the LSD, an effective amount of a compound having Formula II:

Formula II

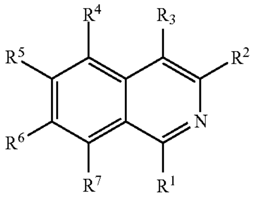

wherein $R^1$ is $NR^8R^9$, $CR^8R^9R^{10}$, or $OR^8$, wherein $R^8$, $R^9$ and $R^{10}$ are each independently H or substituted or unsubstituted aryl (e.g., substituted or unsubstituted phenyl);

$R^2$, $R^3$, $R^4$, $R^6$, and $R^7$ are each independently H, OH, $C_{1-6}$ alkyl, or $C_{1-6}$alkoxy; and $R^5$ is $NR^{11}R^{12}$ or $OR^{10}$, wherein $R^{11}$ and $R^{12}$ are each independently H, OH, substituted or unsubstituted alkyl, or substituted or unsubstituted aryl.

Also provided is a method of treating or preventing a neurodegenerative disease, a neurodevelopmental disorder, a myodegenerative disease, a prion disease or a lysosomal storage disorder (LSD) in a subject, comprising administering to the subject with the neurodegenerative disease, a neurodevelopmental disorder, the myodegenerative disease, the prion disease or the LSD or at risk for developing the neurodegenerative disease, a neurodevelopmental disorder, the myodegenerative disease the prion disease or the LSD, an effective amount of a compound having Formula III:

Formula III

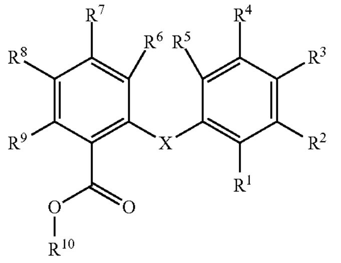

wherein

X is $NR^{11}$, S, or O. $R^{11}$ is H, substituted or unsubstituted alkyl, or substituted or unsubstituted aryl;

$R^1$ is H or $C_1$-$C_6$ alkyl;

$R^2$ is H, OH, halogen (e.g., F, Cl, Br, or I), or $C_1$-$C_6$ alkyl;

$R^3$, $R^4$, $R^5$, $R^6$, $R^7$, $R^8$, and $R^9$ are each independently H, OH, $C_{1-6}$alkyl, or $C_{1-6}$ alkoxy; and $R^{10}$ is H or $C_{1-6}$ alkyl.

Also provided is a method of treating a neurodevelopmental disorder in a subject, comprising administering to the subject with the neurodevelopmental disorder an effective amount of a compound having Formula IV Formula IV

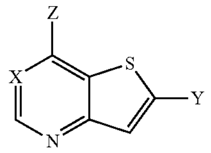

wherein X is N or CH;

Y is $C_{6-10}$ aryl unsubstituted or substituted with $R^1$; or $C_{5-10}$ heteroaryl unsubstituted or substituted with $R^1$, or N-methylpiperazinyl;

$R^1$ is $-(CH_2)_n-R^2$, $-(CH_2)_r-C(O)-R^2$, or $-O(CH_2)-R^2$;

$R^2$ is —H, —CN, halogen, $C_{1-3}$ alkyl, $C_{1-3}$ alkoxy, phenyl, pyridinyl, amino, $C_{1-3}$ alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl, $C_{1-3}$ alkylpipeidinyl, di $C_{1-3}$ alkyl piperidinyl, piperazinyl, $C_{1-3}$ alkylpiperazinyl, $C_{1-4}$ alkoxycarbonylpiperazinyl, or morpholinyl;

Z is heteroaryl, heterocyclyl, or $NR^3R^4$;

$R^3$ and $R^4$ are independently H, $C_{1-3}$ alkyl, $C_{1-3}$ alkoxy, or unsubstituted phenyl, and n is an integer selected from 0 to 3, or an isomer or pharmaceutically acceptable salt thereof.

DESCRIPTION OF THE FIGURES

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 1A (bottom panel) shows that low doses of BK5029 displayed increased toxicity in B35 rat neuroblastoma cells, as measured by 3-(4,5-dimethylthiazol-2-yl)-2,5-diphenyltetrazolium bromide, a tetrazole (MTT) assay. A decreased in MIT is indicative of cell toxicity.

FIG. 1B (bottom panel) shows that no concentration of BK5030 displayed increased toxicity in B35 rat neuroblastoma cells, as measured by MIT assay.

FIG. 1C (bottom panel) shows that no concentration of CL2-296 displayed increased cell toxicity in B35 rat neuroblastoma cells, as measured by MiT assay.

FIG. 1D (bottom panel) shows that 100 uM concentrations of BK5026 displayed increased levels of cell toxicity, as measured by MTT assay.

FIG. 1E (bottom panel) shows that no concentration of BK5018 displayed increased toxicity, as measured by MTT assay.

FIG. 3A (top panel) shows that treatment of B35 rat neuroblastoma cells with Compound 7 (CL-2-287-1) at 100 μM or less did not show increased cell toxicity, as measured by LDH assay. FIG. 3A (bottom panel) shows that treatment of B35 rat neuroblastoma cells with Compound 7 (CL-2-287-1) at 100 μM or less did not show increased cell toxicity, as measured by MT assay.

FIG. 3B (top panel) shows that treatment of B35 rat neuroblastoma cells with Compound 8 (CL-2-287-2) at 100 μM or less did not show increased cell toxicity, as measured by LDH assay. FIG. 3B (bottom panel) shows that treatment of B35 rat neuroblastoma cells with Compound 8 (CL-2-287-2) at 10 μM or less did not show increased cell toxicity, as measured by MIT assay.

DETAILED DESCRIPTION

Figure 1A:
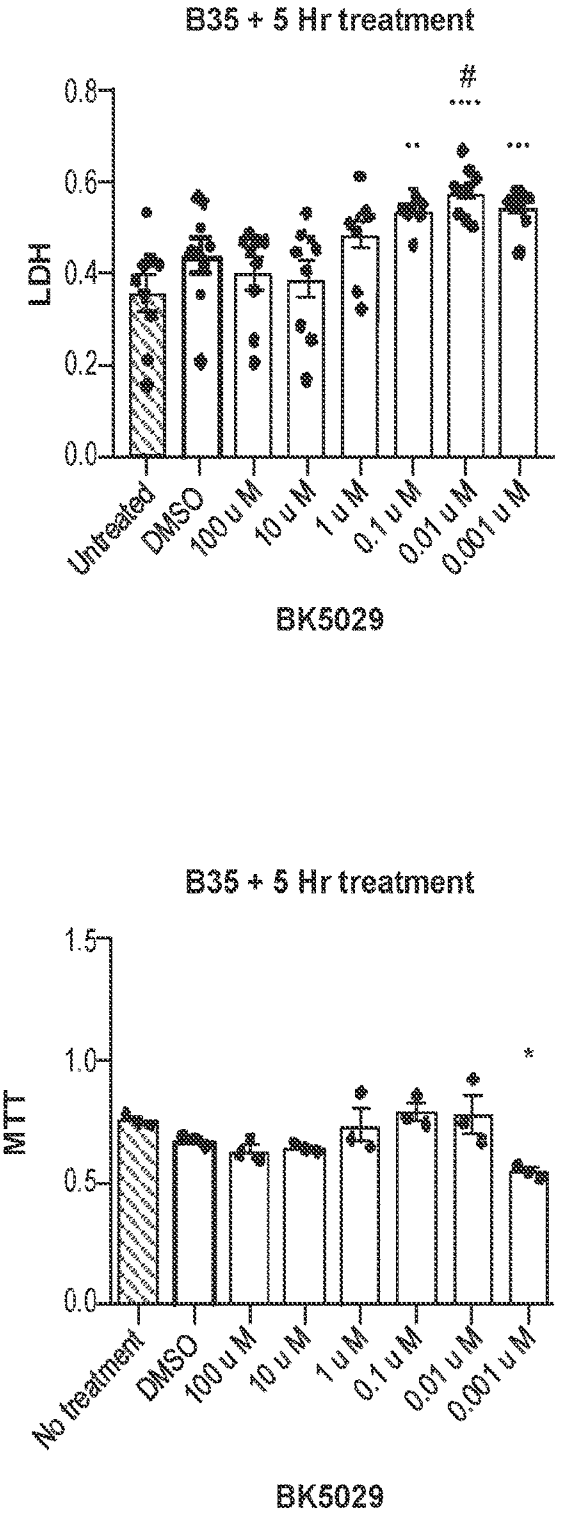
FIG. 1A (top panel) shows that low doses of BK5029 displayed increased toxicity in B35 rat neuroblastoma cells, as measured by lactate dehydrogenase (LDH) assay. An increase in LDH is indicative of cell toxicity.

Provided herein are compositions and methods for treating or preventing a neurodegenerative disease, a neurodevelopmental disease, a myodegenerative disease, a prion disease or a lysosomal storage disease in a subject.

Compounds

In some examples, a class of compounds described herein includes compounds represented by Formula I:

Formula I

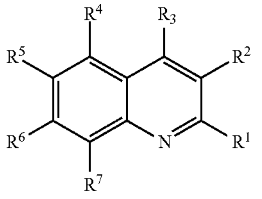

or an isomer or pharmaceutically acceptable salt thereof.

In Formula I, $R^1$ is $NR^8R^9$, $CR^8R^9R^{10}$, or $OR^8$, wherein $R^8$, $R^9$ and $R^{10}$ are each independently H, OH, substituted or unsubstituted aryl (e.g., substituted or unsubstituted phenyl), or substituted or unsubstituted alkyl, cycloalkyl, heteroalkyl, cycloheteroalkyl, or heteroaryl. In some examples, $R^8$, $R^9$ and $R^{10}$ are each independently H, OH, $C_1$-$C_3$ alkyl ester optionally substituted with benzyl, or substituted or unsubstituted phenyl.

Also in Formula I, $R^2$, $R^4$, $R^5$, $R^6$, and $R^7$ are each independently H, OH, halogen, $C_{1-6}$alkyl, or $C_{1-6}$ alkoxy. In some examples, $R^6$ is halogen (e.g., F, Cl, Br, or I). In some examples, $R^2$. $R^4$, $R^5$, and $R^7$ are each independently not halogen.

Additionally, in Formula I, $R^3$ is $NR^{11}R^{12}$ or $OR^{11}$, wherein $R^{11}$ and $R^{12}$ are each independently H, OH, substituted or unsubstituted aryl (e.g., substituted or unsubstituted phenyl), or substituted or unsubstituted alkyl, cycloalkyl, heteroalkyl, cycloheteroalkyl, or heteroaryl. In some examples, $R^{11}$ and $R^{12}$ are each independently $C_1$-$C_3$ alkyl ester optionally substituted with benzyl, phenyl, or phenyl substituted with $C_1$-$C_6$ alkyl or $C_1$-$C_6$ alkoxy.

In some examples of Formula I, $R^3$ is $NHR^{11}$ wherein $R^{11}$ is phenyl substituted with methyl as shown below:

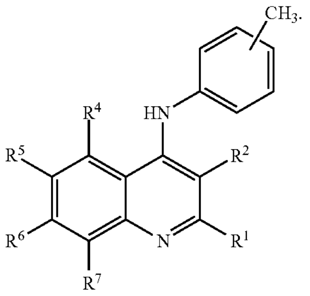

In some examples of Formula I, $R^3$ is $NHR^{11}$ where $R^{11}$ is phenyl substituted with methoxy as shown below:

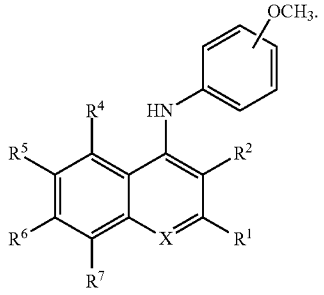

In some examples of Formula I, $R^3$ is $OR^{11}$ wherein $R^{11}$ is phenyl substituted with methyl as shown below:

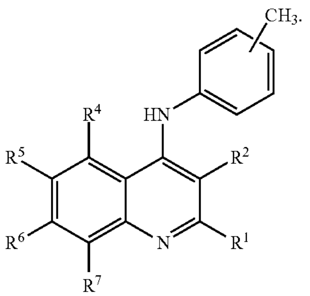

Examples of Formula I include the following compounds:

Compound 1

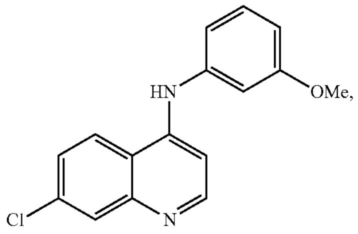

(BK5018)

Compound 2

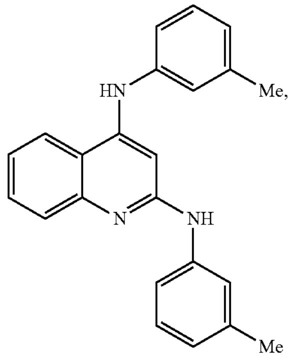

(BK5026)

Compound 3

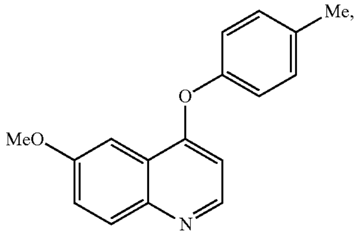

(BK5029)

Compound 4

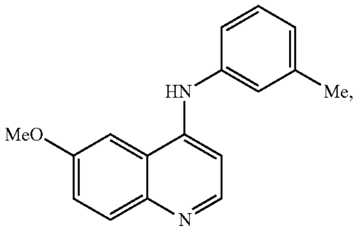

and (BK5030)

Compound 5

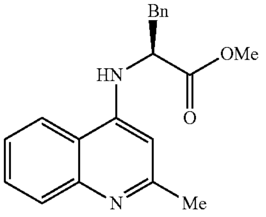

(DH016)

In some examples, a class of compounds as described herein includes compounds represented by Formula III:

Formula II

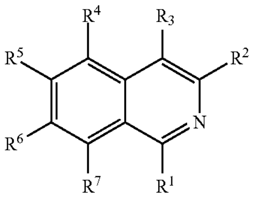

or an isomer or pharmaceutically acceptable salt thereof.

In Formula I, $R^1$ is $NR^8R^9$, $CR^8R^9R^{10}$, or $OR^8$, wherein $R^8$, $R^9$ and $R^{10}$ are each independently H or substituted or unsubstituted aryl (e.g., substituted or unsubstituted phenyl). In some examples, $R^8$, $R^9$ and $R^{10}$ are each independently H phenyl, or phenyl substituted with $C_1$-$C_6$ alkyl or $C_1$-$C_6$ alkoxy.

Also in Formula M, $R^2$, $R^3$, $R^4$, $R^6$, and $R^7$ are each independently H, OH, $C_{1-6}$ alkyl, or $C_{1-6}$ alkoxy.

Additionally, in Formula II, $R^5$ is $NR^{11}R^{12}$ or $OR^{10}$, wherein $R^{11}$ and $R^{12}$ are each independently H, OH, substituted or unsubstituted alkyl, or substituted or unsubstituted aryl. In some examples, $R^{11}$ and $R^{12}$ are each independently H, OH, phenyl, or phenyl substituted with $C_1$-$C_6$ alkyl or $C_1$-$C_6$ alkyoxy.

An example of Formula II includes the following compound:

Compound 6

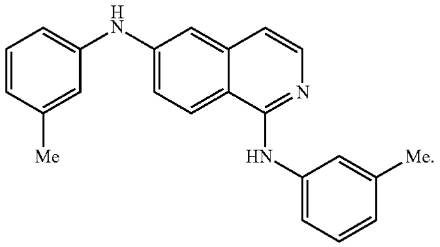

(CL2-296)

In some examples, a class of compounds as described herein includes compounds represented by Formula I:

Formula III

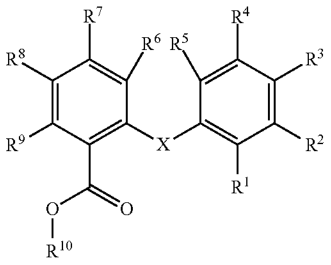

or an isomer or pharmaceutically acceptable salt thereof.

In Formula III, X is $NR^{11}$, S, or O. $R^{11}$ is H, substituted or unsubstituted alkyl, or substituted or unsubstituted aryl.

Also in Formula III, $R^1$ is H or $C_1$-$C_6$ alkyl.

Additionally in Formula II, $R^2$ is H, OH, halogen (e.g., F, CL Br, or I), or $C_1$-$C_6$ alkyl.

Further, in Formula III, $R^3$, $R^4$, $R^5$, $R^6$, $R^7$, $R^8$, and $R^9$ are each independently H, OH, $C_{1-6}$ alkyl, or $C_{1-6}$ alkoxy.

Also in Formula III, $R^{10}$ is —H or $C_{1-6}$ alkyl.

Examples of Formula III include the following compounds:

Compound 7

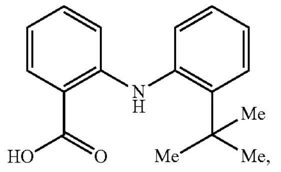

(CL2-287-1)

Compound 8

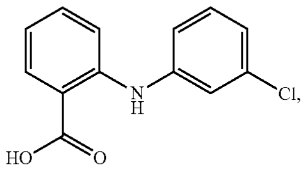

(CL2-287-2)

or an isomer or pharmaceutically acceptable salt thereof.

In some examples, a class of compounds described herein includes compounds represented by Formula IV:

I

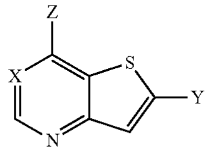

or an isomer or pharmaceutically acceptable salt thereof.

In Formula IV, X is N or CH.

Also, in Formula IV, Y is $C_{6-10}$ aryl unsubstituted or substituted with $R^1$; or $C_{5-10}$ heteroaryl unsubstituted or substituted with $R^1$, or N-methylpiperazinyl.

Also, in Formula IV, $R^1$ is $—(CH_2)_n—R^2$, $—(CH_2)_n—C(O)—R^2$, or $—O(CH_2)_n—R^2$.

Additionally, in Formula IV, $R^2$ is —H, —CN, halogen, $C_{1-3}$ alkyl, $C_{1-3}$ alkoxy, phenyl, pyridinyl, amino, $C_{1-3}$alkyl amino, di $C_{1-3}$alkyl amino, hydroxyl $C_{1-3}$alkyl amino, carboxy $C_{1-3}$ alkyl amino, $C_{3-6}$cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl. $C_{1-3}$ alkylpiperidinyl, di $C_{1-3}$ alkyl piperidinyl, piperazinyl. $C_{1-3}$ alkylpiperazinyl, $C_{1-4}$ alkoxycarbonylpiperazinyl, or morpholinyl.

Z is heteroaryl, heterocyclyl, or $NR^3R^4$.

Also, in Formula IV, $R^3$ and $R^4$ are independently selected from H, $C_{1-3}$ alkyl $C_{1-3}$ alkoxy, or unsubstituted phenyl, and n is an integer selected from 0 to 3.

In some examples of Formula IV, Y is benzyl substituted with $R^1$:

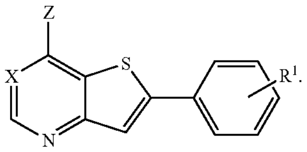

In some examples of Formula IV, Y is benzyl substituted with $R^1$ in the meta position:

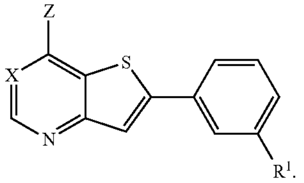

In some examples of Formula IV, Z is $NR^3R^4$, $R^3$ is benzyl or H, $R^4$ is benzyl or H, and Y is benzyl substituted with $R^1$:

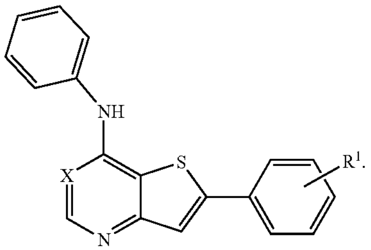

In some examples of Formula IV, Z is $NR^3R^4$, $R^3$ is benzyl or H. $R^4$ is benzyl or H, and Y is benzyl substituted with $R^1$ in the meta position:

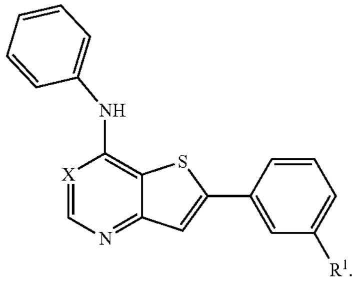

In some examples of Formula IV, Z is morpholinyl and Y is benzyl substituted with $R^1$:

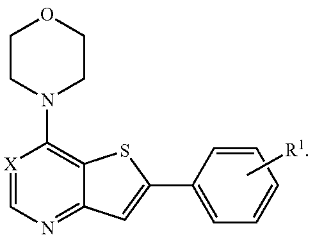

In some examples of Formula IV, Z is morpholinyl and Y is benzyl substituted with $R^1$ in the meta position:

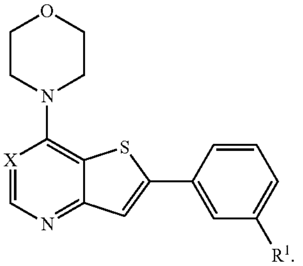

A compound of Formula IV is Compound 9 (BK40197):

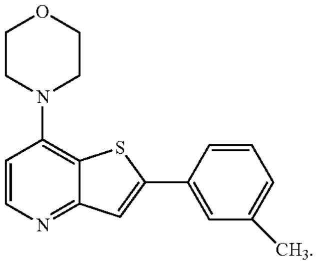

4-(2-(m-tolyl)thieno[3,2-b]pyridin-7-yl)morpholine

Another compound of Formula IV is Compound 10 (BK40193):

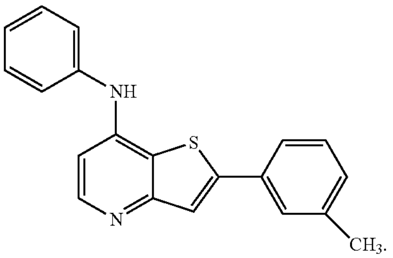

N-phenyl-2-(m-tolyl)thieno[3,2-b]pyridin-7-amine

In some examples of Formula IV, the compound does not comprise one or more halogen atoms. In some examples of Formula IV, Y is 2-m-toluyl. In some examples of Formula I, Z is heterocyclyl. In some examples of Formula IV, Z is morpholin-1-yl. In some examples of Formula IV, $R^3$ is H and $R^4$ is unsubstituted phenyl.

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

The term alkoxy as used herein is an alkyl group bound through a single, terminal ether linkage. The term hydroxy as used herein is represented by the formula OH.

The terms amine or amino as used herein are represented by a formula $NR^xR^y$, where $R^x$ and $R^y$ can each be a substitution group as described herein, such as hydrogen, an alkyl, a cycloalkyl, a halogenated alkyl, alkenyl, or alkynyl group described above.

The alkoxy, amino, alkyl, alkenyl, alkynyl, or carbonyl molecules used herein can be substituted or unsubstituted. As used herein, the term substituted includes the addition of an alkoxy, amino, alkyl, alkenyl, alkynyl, or carbonyl group to a position attached to the main chain of the alkoxy, amino, alkyl, alkenyl, alkynyl, or carbonyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkoxy, amino, alkyl, alkenyl, alkynyl, or carbonyl has a full complement of hydrogens, i.e., commensurate with its saturation level, with no substitutions, e.g., linear decane ($-(CH_2)_9-CH_3$).

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

Optionally, the compound of Formula I, Formula II, Formula I or Formula IV inhibits one or more receptor tyrosine kinases selected from the group consisting of Abl, PDGFRα, PDGFRβ, DDR 1, DDR2, cKIT, arginase II, Src, Fyn, VEGFR and Zac. In some examples, the compound of Formula I selectively inhibits Abl, PDGFRα, PDGFRβ, DDR 1. DDR2, cKIT, arginase II, Src, Fyn or VEGR or Zac. In some examples, the compound having Formula I inhibits DDR 1 and/or DDR2. For example, and not to be limiting. Compound 1, Compound 2 Compound 3, Compound 4, Compound 5, Compound 6, Compound 7, Compound 8, Compound 9 or Compound 10 can be used to inhibit DDR1 and/or DDR2. In another example, the compound having Formula I, Formula II, Formula III or Formula IV, for example, Compound 1, Compound 2 Compound 3, Compound 4, Compound 5, Compound 6, Compound 7, Compound 8, Compound 9 or Compound 10, selectively inhibits DDR 1 or DDR2.

As used herein, the term pharmaceutically acceptable salt refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds provided herein, for example, pharmaceutically acceptable salts of nilotinib, bosutinib pazopanib and a compound of Formula I, Formula II or Formula I, include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate. 3-phenylpropionate, phosphate, pivalate, propionate, stearate, succinate, sulfate, tartrate, thiocyanate, p-toluenesulfonate, trifluoroacetic acid, undecanoate, valerate salts, and the like.

The compounds described herein can be prepared in a variety of ways. The compounds can be synthesized using various synthetic methods, including those provided in the Examples. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I, Formula II, Formula III or Formula IV, include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Any of the compounds described herein can be modified to enhance blood-brain barrier permeability. Optionally, one or more of the compounds described herein can be administered with an agent that enhances the blood brain barrier permeability of the compound(s).

Methods for Treating or Preventing Neurodegenerative Diseases, Myodegenerative Diseases or Prion Diseases Provided herein are methods of treating or preventing a neurodegenerative disease, a myodegenerative disease or a prion disease. The neurodegenerative disease or disorder can be a neurodegenerative disease of the central nervous system. These include, but are not limited to, amyotrophic lateral sclerosis, Alzheimer's disease, frontotemporal dementia. TDP-43 pathologies, including frontotemporal dementia with TDP-43, frontotemporal dementia linked to chromosome-17, amyloidosis, Pick's disease, Huntington's disease, mild cognitive impairment, an α-synucleinopathy (e.g., Parkinson's disease, Lewy body disease), multiple sclerosis, Glial Cytoplasmic Inclusions, including multiple system atrophy, chronic traumatic encephalopathies, a Tauopathy, progressive supranuclear palsy, and corticobasal degeneration. The neurodegenerative disease can also be a secondary neurodegenerative disease induced by a traumatic brain injury, stroke or an infection, for example, a bacterial or a viral infection (e.g., HIV, Herpes simplex virus (HSV)).

Myodegenerative diseases or disorders include but are not limited to a dystrophy (for example, muscular dystrophy), a myopathy (for example, nemaline myopathy, mulit/minicore myopathy, centronuclear myopathy, mitochondrial myopathy, metabolic myopathy, etc.) or myotonia (for example, myotonia congenita, paramyotonia congenital or myotonic dystrophy).

Prion diseases or disorders include but are not limited to Creutzfeldt-Jakob Disease, Variant Creutzfeldt-Jakob Disease, Gerstmann-Straussler-Scheinker Syndrome, Fatal Familial Insomnia, Kuru, Bovine Spongiform Encephalopathy, Chronic Wasting Disease and Scrapie, to name a few.

The methods comprise administering to the subject with the neurodegenerative disease, myodegenerative disease or prion disease, or at risk of developing the neurodegenerative disease, the myodegenerative disease or the prion disease an effective amount of a compound having Formula I:

Formula I

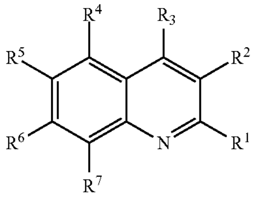

or an isomer or pharmaceutically acceptable salt thereof, wherein $R^1$ is H, $NR^8R^9$, $CR^8R^9R^{10}$, or $OR^8$;

$R^8$, $R^9$ and $R^{10}$ are each independently H, OH, substituted or unsubstituted aryl(e.g., substituted or unsubstituted phenyl), or substituted or unsubstituted alkyl, cycloalkyl, heteroalkyl, cycloheteroalkyl, or heteroaryl;

$R^2$, $R^4$, $R^5$, $R^6$, and $R^7$ are each independently H, OH, halogen, $C_{1-6}$ alkyl, or $C_{1-6}$ alkoxy. In some examples, $R^6$ is halogen (e.g., F, Cl, Br, or I); and $R^3$ is $NR^{11}R^{12}$ or $OR^{11}$, wherein $R^{11}$ and $R^{12}$ are each independently H, OH, substituted or unsubstituted aryl (e.g., substituted or unsubstituted phenyl), or substituted or unsubstituted alkyl alkyl, cycloalkyl, heteroalkyl, cycloheteroalkyl, or heteroaryl.

In some methods, $R^2$, $R^4$, $R^5$, and $R^7$ are each independently not halogen.

In some methods, $R^8$ and $R^9$ are each independently H, OH, $C_1$-$C_3$ alkyl ester optionally substituted with benzyl, or substituted or unsubstituted phenyl.

In some methods, $R^{11}$ and $R^{12}$ are each independently $C_1$-$C_3$ alkyl ester optionally substituted with benzyl, phenyl, or phenyl substituted with $C_1$-$C_6$ alkyl or $C_1$-$C_6$ alkoxy.

In some methods. $R^3$ is $NHR^1$, wherein $R^{11}$ is phenyl substituted with methyl as shown below:

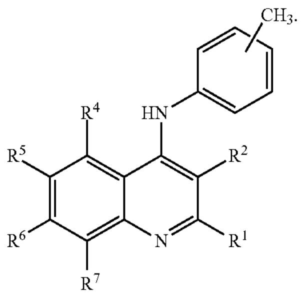

In some methods, $R^3$ is $NHR^{11}$ where $R^{11}$ is phenyl substituted with methoxy as shown below:

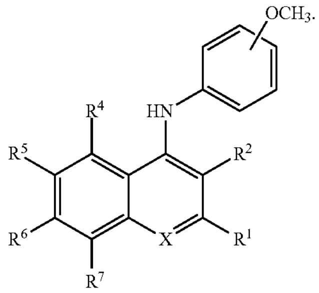

In some methods. $R^3$ is $OR^{11}$ wherein $R^{11}$ is phenyl substituted with methyl as shown below:

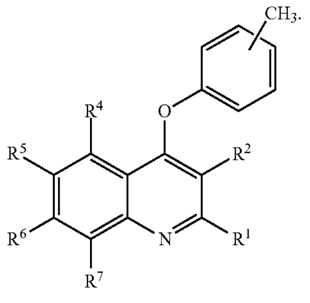

Examples of Formula I include the following compounds:

Compound 1

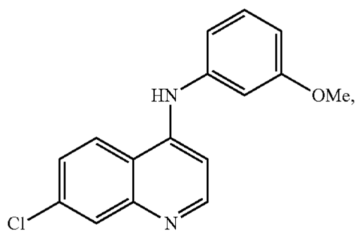

(BK5018)

Compound 2

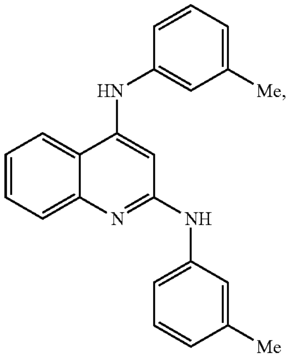

(BK5026)

Compound 3

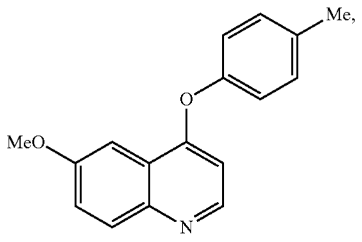

(BK5029)

Compound 4

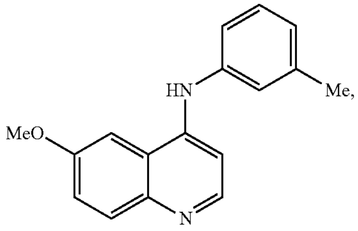

and (BK5030)

Compound 5

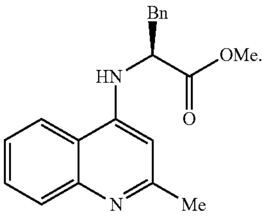

(DH016)

Some methods comprise administering to the subject with the neurodegenerative disease, myodegenerative disease or prion disease, or at risk of developing the neurodegenerative disease, the myodegenerative disease or the prion disease an effective amount of a compound having Formula II:

Formula II

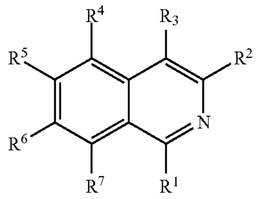

or an isomer or pharmaceutically acceptable salt thereof. wherein $R^1$ is $NR^8R^9$, $CR^8R^9R^{10}$, or $OR^8$;

$R^8$, $R^9$ and $R^{10}$ are each independently H or substituted or unsubstituted aryl(e.g., substituted or unsubstituted phenyl); In some examples, $R^8$, $R^9$ and $R^{10}$ are each independently H phenyl, or phenyl substituted with $C_1$-$C_6$ alkyl or $C_1$-$C_6$ alkoxy;

$R^2$, $R^3$, $R^4$, $R^6$, and $R^7$ are each independently H, OH, $C_{1-6}$ alkyl, or $C_{1-6}$alkoxy;

$R^5$ is $NR^{11}R^{12}$ or $OR^{10}$; and $R^{11}$ and $R^{12}$ are each independently H, OH, substituted or unsubstituted alkyl, or substituted or unsubstituted aryl.

In some methods, $R^8$, $R^9$ and $R^{10}$ are each independently H phenyl, or phenyl substituted with $C_1$-$C_6$ alkyl or $C_1$-$C_6$ alkoxy.

In some methods, $R^{11}$ and $R^{12}$ are each independently H, OH, phenyl, or phenyl substituted with $C_1$-$C_6$ alkyl or $C_1$-$C_6$ alkyoxy.

An example of Formula II includes the following compound:

Compound 6

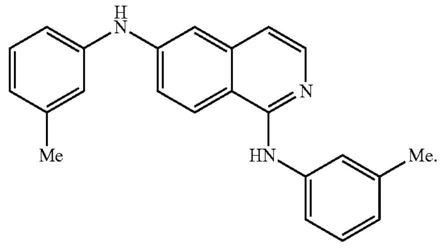

(CL2-296)

Other methods comprise administering to the subject with the neurodegenerative disease, myodegenerative disease or prion disease, or at risk of developing the neurodegenerative disease, the myodegenerative disease or the prion disease an effective amount of a compound having Formula II:

Formula III

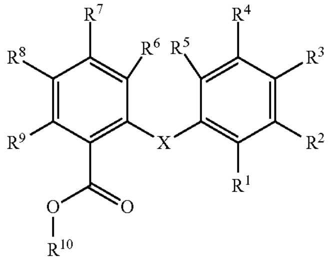

or an isomer or pharmaceutically acceptable salt thereof, wherein

X is $NR^{11}$, S, or O;

$R^{11}$ is H, substituted or unsubstituted alkyl, or substituted or unsubstituted aryl;

$R^1$ is H or $C_1$-$C_6$ alkyl;

$R^2$ is H, OH, halogen (e.g., F, Cl, Br, or I), or $C_1$-$C_6$ alkyl;

$R^3$, $R^4$, $R^5$, $R^6$, $R^7$, $R^8$, and $R^9$ are each independently H, OH, $C_{1-4}$alkyl, or $C_{1-4}$alkoxy; and $R^{10}$ is —H or $C_{1-6}$ alkyl.

Examples of Formula III include the following compounds:

Compound 7

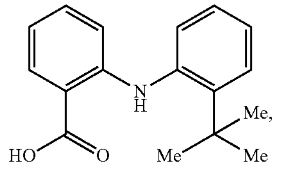

(CL2-287-1)

Compound 8

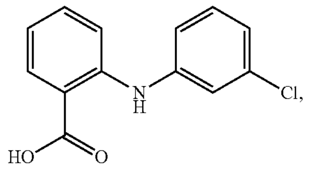

(CL2-287-2)

or an isomer or pharmaceutically acceptable salt thereof.

The methods provided herein optionally include selecting a subject with a neurodegenerative disease, a myodegenerative disease or a prion disease or at risk for developing a neurodegenerative disease, a myodegenerative disease or a prion disease. One of skill in the art knows how to diagnose a subject with or at risk of developing a neurodegenerative disease, a myodegenerative disease or a prion disease. For example, one or more of the follow tests can be used: a genetic test (e.g., identification of a mutation in TDP-43 gene) or familial analysis (e.g., family history), central nervous system imaging (e.g., magnetic resonance imaging and positron emission tomography), electroencephalography, clinical or behavioral tests (e.g., assessments of muscle weakness, tremor, gait, or memory), or laboratory tests.

The method optionally further includes administering a second therapeutic agent to the subject. The second therapeutic agent is selected from the group consisting of levadopa, a dopamine agonist, an anticholinergic agent, a cholinergic agent (e.g., 5-hydroxytryptamine (5-HT) inhibitors), a monoamine oxidase inhibitor, a COMT inhibitor, donepezil, memantine, risperidone, amantadine, rivastigmine, an NMDA antagonist, an acetycholinesterase inhibitor, a cholinesterase inhibitor, riluzole, an anti-psychotic agent, an antidepressant, a glucocorticoid (for example, prednisone), a tyrosine kinase inhibitor (e.g., nilotinib, bosutinib, imatinib, pazopanib, etc.), and tetrabenazine. The second therapeutic agent or therapy can be administered to the subject prior to, simultaneously with, or subsequent to administration of the compound having Formula I.

In the methods where a tyrosine kinase inhibitor is administered as a second therapeutic agent, the tyrosine kinase inhibitor can be a tyrosine kinase inhibitor that does not inhibit a tyrosine kinase receptor that is inhibited by the compound of Formula I or has decreased selectivity for a tyrosine kinase receptor, as compared to a compound of Formula I.

Also provided herein is a method of inhibiting or preventing toxic protein aggregation in a neuron and/or rescuing a neuron from degeneration. As used herein, references to inhibiting, decreasing or reducing include a change of 10%, 20%, 30%, 40%, 50%, 60%, 70%, 80%, 90% or greater as compared to a control level.

The method includes contacting the neuron with an effective amount of a compound of Formula I, Formula II or Formula III, as described herein. Optionally, the compound having Formula I, Formula II or Formula III is selected from the group consisting of Compound 1, Compound 2, Compound 3. Compound 4, Compound 5. Compound 6, Compound 7 and Compound 8. The toxic protein aggregate optionally comprises one or more of an amyloidogenic protein, alpha-synuclein, tau, or TDP-43. By amyloidogenic protein is meant a peptide, polypeptide, or protein that has the ability to aggregate. An example of an amyloidogenic protein is β-amyloid. The contacting is performed in vivo or in vitro. The in vivo method is useful in treating a subject with or at risk of developing toxic protein aggregates and comprises administering the compound of Formula I to the subject as described below. The in vino method is useful, for example, in treating neural cells prior to transplantation. In such case, the compound of Formula I is generally added to a culture medium. Optionally, the target neurons are contacted with a second therapeutic agent as described above.

Methods for Treating or Preventing Lysosomal Storage Disorders (LSD)

Also provided are methods for treating or preventing a LSD in a subject. The methods comprise administering to the subject with the LSD or at risk of developing the LSD an effective amount of a compound having Formula I:

Formula I

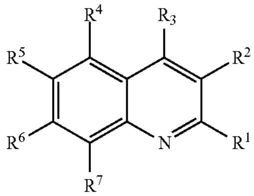

or an isomer or pharmaceutically acceptable salt thereof, wherein $R^1$ is H, $NR^8R^9$, $CR^8R^9R^{10}$, or $OR^8$;

$R^8$, $R^9$ and $R^{10}$ are each independently H, OH, substituted or unsubstituted aryl (e.g., substituted or unsubstituted phenyl), or substituted or unsubstituted alkyl, cycloalkyl, heteroalkyl, cycloheteroalkyl, or heteroaryl.

$R^2$, $R^4$, $R^5$, $R^6$, and $R^7$ are each independently H, OH, halogen, $C_{1-6}$ alkyl, or $C_{1-6}$ alkoxy;

$R^3$ is $NR^{11}R^{12}$ or $OR^{11}$, wherein $R^{11}$ and $R^{12}$ are each independently H, OH, substituted or unsubstituted aryl (e.g., substituted or unsubstituted phenyl), or substituted or unsubstituted alkyl alkyl, cycloalkyl, heteroalkyl, cycloheteroalkyl, or heteroaryl.

In some methods, $R^6$ is halogen (e.g., F, Cl, Br, or I), In some examples, $R^2$, $R^4$, $R^5$, and $R^7$ are each independently not halogen.

In some methods, $R^8$ and $R^9$ are each independently H, OH, $C_1$-$C_3$ alkyl ester optionally substituted with benzyl, or substituted or unsubstituted phenyl.

In some methods, $R^{11}$ and $R^{12}$ are each independently $C_1$-$C_3$ alkyl ester optionally substituted with benzyl, phenyl, or phenyl substituted with $C_1$-$C_6$ alkyl or $C_1$-$C_6$ alkoxy.

In some methods, $R^3$ is $NHR^{11}$, wherein $R^{11}$ is phenyl substituted with methyl as shown below:

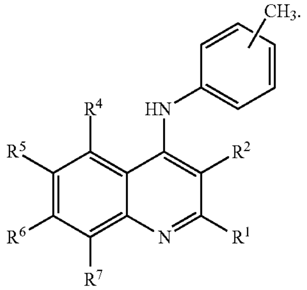

In some methods, $R^3$ is $NHR^{11}$ where $R^{11}$ is phenyl substituted with methoxy as shown below:

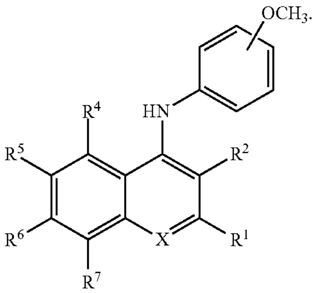

In some methods, $R^3$ is $OR^{11}$ wherein $R^{11}$ is phenyl substituted with methyl as shown below:

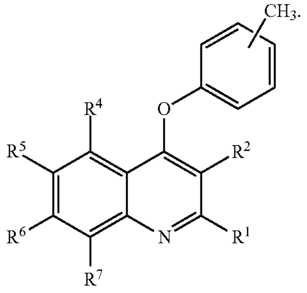

Examples of Formula I include the following compounds:

Compound 1

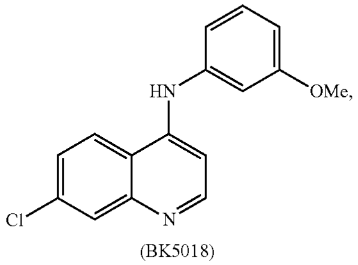

(BK5018)

-continued

Compound 2

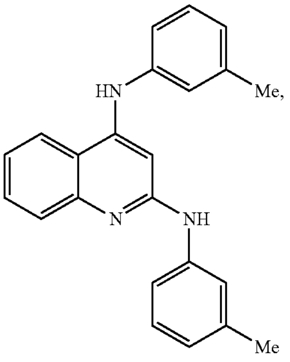

(BK5026)

Compound 3

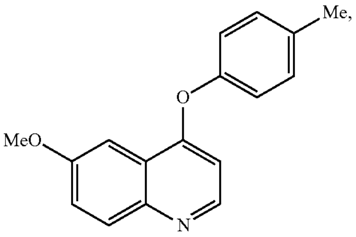

(BK5029)

Compound 4

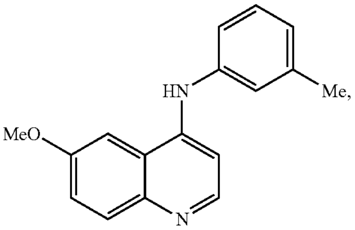

and (BK5030)

Compound 5

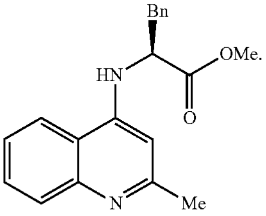

(DH016)

Some methods comprise administering to the subject with the LSD or at risk of developing the LSD an effective amount of a compound having Formula II:

Formula II

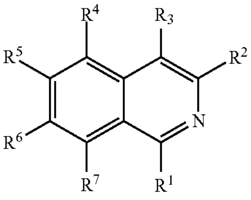

or an isomer or pharmaceutically acceptable salt thereof.

wherein $R^1$ is $NR^8R^9$, $CR^8R^9R^{10}$, or $OR^8$;

$R^8$, $R^9$ and $R^{10}$ are each independently H or substituted or unsubstituted aryl (e.g., substituted or unsubstituted phenyl); In some examples $R^8$, $R^9$ and $R^{10}$ are each independently H phenyl, or phenyl substituted with $C_1$-$C_6$ alkyl or $C_1$-$C_6$ alkoxy;

$R^2$, $R^3$, $R^4$, $R^6$, and $R^7$ are each independently H, OH, $C_{1-6}$ alkyl, or $C_{1-6}$ alkoxy;

$R^5$ is $NR^{11}R^{12}$ or $OR^{10}$; and $R^{11}$ and $R^{12}$ are each independently H, OH, substituted or unsubstituted alkyl, or substituted or unsubstituted aryl.

In some methods, $R^8$, $R^9$ and $R^{10}$ are each independently H phenyl, or phenyl substituted with $C_1$-$C_6$ alkyl or $C_1$-$C_6$ alkoxy.

In some methods, $R^{11}$ and $R^{12}$ are each independently H, OH, phenyl, or phenyl substituted with $C_1$-$C_6$ alkyl or $C_1$-$C_6$ alkyoxy.

An example of Formula II includes the following compound

Compound 6

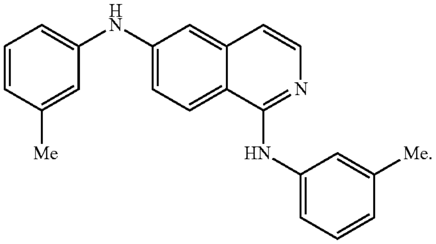

(CL2-296)

Other methods comprise administering to the subject with the LSD or at risk of developing the LSD an effective amount of a compound having Formula III:

Formula III

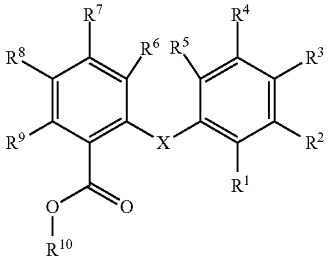

or an isomer or pharmaceutically acceptable salt thereof, wherein

X is $NR^{11}$, S, or O;

$R^{11}$ is H, substituted or unsubstituted alkyl, or substituted or unsubstituted aryl;

$R^1$ is H or $C_1$-$C_6$ alkyl;

$R^2$ is H, OH, halogen (e.g., F, Cl, Br, or I), or $C_1$-$C_6$ alkyl;

$R^3$, $R^4$, $R^5$, $R^6$, $R^7$, $R^8$, and $R^9$ are each independently H, OH, $C_{1-6}$ alkyl, or $C_{1-6}$ alkoxy; and $R^{10}$ is —H or $C_{1-6}$ alkyl.

Examples of Formula III include the following compounds:

Compound 7

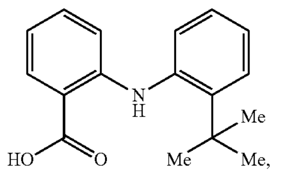

(CL2-287-1)

Compound 8

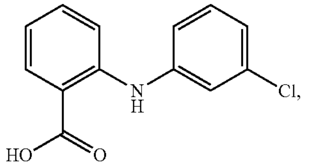

(CL2-287-2)

or an isomer or pharmaceutically acceptable salt thereof.

Optionally, the compound of Formula I, Formula II or Formula III inhibits one or more receptor tyrosine kinases selected from the group consisting of Abi, PDGFRα, PDGFRβ, DDR 1, DDR2, cKIT, arginase II, Src, Fyn, VEGFR and Zac. In some examples, the compound of Formula I selectively inhibits Abl, PDGFRα, PDGFRβ, DDR 1, DDR2, cKIT, arginase II, Src, Fyn or VEGR or Zac. In some examples, the compound having Formula I inhibits DDR 1 and/or DDR2. For example, and not to be limiting, Compound 1, Compound 2 Compound 3, Compound 4, Compound 5, Compound 6, Compound 7 or Compound 8 can be used to inhibit DDR1 and/or DDR2. In another example, the compound having Formula I, Formula II or Formula III for example. Compound 1, Compound 2 Compound 3, Compound 4, Compound 5, Compound 6, Compound 7 or Compound 8 selectively inhibits DDR 1 or DDR2.

LSDs are inherited metabolic disorders that result from defects in lysosomal function. In the majority of cases, LSDs are caused by a deficiency of specific enzymes responsible for degradation of lipids and glycoproteins present in lysosomes. In some cases, defective non-enzymatic lysosomal proteins or non-lysosomal proteins involved in lysosomal biogenesis cause LSDs. The progressive lysosomal accumulation of undegraded metabolites results in generalized cell and tissue dysfunction, and, therefore, multi-systemic pathology. LSDs that can be treated or prevented using the methods provided herein include, but are not limited to, Mucopolysaccharidosis Type I (for example, Hurler syndrome, Hurler-Scheie syndrome and Scheie syndrome), Mucopolysaccharidosis Type I (for example, Hunter syndrome), Mucopolysaccharidosis Type I (for example, Sanfillipo syndrome A, Sanfillipo syndrome B, Sanfillipo syndrome C and Sanfillipo syndrome D), Mucopolysaccharidosis Type IV (for example, Morquio syndrome A and Morquio syndrome B), Mucopolysaccharidosis Type VI (for example, Maroteaux-Lamy syndrome), Mucopolysaccharidosis Type VII (for example, Sly syndrome), Mucopolysaccharidosis Type IX (for example, Natowicz syndrome), Pseudo-Hurler polydystrophy, Tay-Sachs, Gaucher disease, Niemann-Pick disease, Fucosidosis, Galactosialidosis, Globoid-cell leukodystrophy, $G_{M1}$ Gangliosidosis, $G_{M2}$ Gangliosidosis, α-Mannosidosis, Metachromatic leukodystrophy and Pompe disease. The LSDs provided herein are examples of diseases or disorders associated with decreased lysosomal clearance.

Also provided are methods of promoting lysosomal clearance in one or more cells of a subject comprising administering to the subject that has a disorder associated with decreased lysosomal clearance an effective amount of a compound having Formula I. Optionally, the compound having Formula I, Formula II or Formula III is Compound 1, Compound 2, Compound 3, Compound 4, Compound 5, Compound 6, Compound 7 or Compound 8. As used throughout, lysosomal clearance is a process by which accumulating lipids, proteins, glycoproteins or a combination thereof are metabolized or degraded in the lysosome of one or more cells in the subject. A decrease in lysosomal clearance means a decrease in degradation of lipids, proteins and/or glycoproteins in the lysosome of one or more cells of the subject as compared to a control, for example as compared to lysosomal clearance in one or more cells of a healthy subject. Any disorder associated with decreased lysosomal clearance can be treated using the methods provided herein, including, but limited to, any of the LSDs set forth throughout. As used herein, references to promoting or increasing include a change of 10%, 20%, 30%, 40%, 50%, 60%, 70%, 80%, 90% 100%, 200%, 400% or greater as compared to a control level. Optionally, promoting lysosomal clearance decreases the amount of a lipid, a protein, a glycoprotein or a combination thereof in existing aggregates in the lysosome of one or more cells in a subject. Optionally, promoting lysosomal clearance inhibits or prevents formation of aggregates comprising a lipid, a protein, a glycoprotein or a combination thereof in the lysosome of one or more cells in a subject. Optionally, promoting lysosomal clearance decreases the amount of time required to degrade or metabolize a lipid, a protein, a glycoprotein or a combination thereof in one or more cells of the subject as compared to a control.

Optionally, in the methods provided herein, the effective amount of a compound having Formula I, Formula II or Formula III inhibits or prevents toxic substance aggregation or accumulation in one or more cells of the subject as compared to a control. As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination of the toxic substance in one or more cells of the subject. Optionally, the one or more cells are brain cells, cells in one or more peripheral tissues of the subject, or a combination thereof. Optionally, the brain cells can be neurons and/or glial cells. In the methods provided herein, a toxic substance that can aggregate or accumulate in cells can be one or more of a lipid, a protein or a glycoprotein. The toxic substance(s) can increase cell damage and/or increase cell death in one or more cells of the subject. In the methods provided herein, the toxic substance(s) can be in the lysosome or elsewhere in one or more cells of the subject. For example, and not to be limiting, LSDs characterized by an accumulation of lipids in the cells of a subject include, but are not limited to, sphingolipidoses (including Gaucher's and Niemann-Pick diseases), gangliosidosis (including Tay-Sachs disease), leukodystrophies; mucopolysaccharidoses (including Hunter syndrome and Hurler disease), glycoprotein storage disorders, mucolipidoses, and glycogen storage disease type II (Pompe disease).

Lipids and glycoproteins that accumulate in sphingolipidoses include sphingomyelin in brain and red blood cells (Nieman Pick Disease); glycoplipids, including ceramide trihexoside, in brain heart and kidney (Fabry disease); galactocerebroside in oligondendrocytes (Krabbe disease); glucocerebrosides in red blood cells, spleen and liver (Gaucher disease); GM2 gangliosides in neurons (Tay-Sachs disease) and Sandhoff disease; GM1 gangliosides; and sulfatide compounds in neural tissue (metachromatic leukodystrophy).

Lysosomal storage diseases also include mucopolysaccharidoses (MP) that have a deficiency in one or more lysosomal enzymes, for example, α-L-iduronidate (Hurler disease, Scheie syndrome and Hurler Schei syndrome); iduronate sulphate (hunter disease) heparan sulfate (Sanfilipo type A), N-acetyl-α-D-glucosamine (Sanfilipo type B). CoA-α-glucosaminide-N-aceteltytranfer (Sanfilipo type C), N-Acetyl-α-D-glucosaminide-6-sulfate (Sanfilipo type D and Morquio syndrome type A), B-galactose (Morquio syndrome type B) and N-acetylegalatosamine (Maroteaus-Lamy disease) but all of these MPs diseases are a result of lysosomal accumulation of heparan sulfate, dermatan sulfate or keratan sulfate. Glycogen storage diseases (i.e Pompe disease) result from storage of sugars and phosphorylated sugars in the lysosomes.

The methods provided herein optionally include selecting a subject with a LSD. One of skill in the art knows how to diagnose a subject with a LSD. For example, one or more of the following tests can be used: a genetic test (e.g., identification of a mutation associated with a LSD) or familial analysis (e.g., family history, genetic testing of parents), central nervous system imaging (e.g., magnetic resonance imaging and positron emission tomography), clinical or behavioral tests (e.g., assessments to identify mood disorders, aggressiveness and/or cognitive abnormalities), or laboratory tests (e.g, blood and/or trine tests to identify abnormal levels of metabolites or enzymatic deficiencies).

The methods provided herein optionally further include administering an effective amount of a second therapeutic agent or therapy to the subject. The second therapeutic agent or therapy can be administered to the subject prior to, simultaneously with, or subsequent to administration of the compound of Formula I, Formula II or Formula III. The second therapeutic agent or therapy is selected from the group consisting of an enzyme, hematopoietic stem cells, a bone marrow transplant, gene therapy or a small molecule. For example, and not to be limiting. LSDs associated with an enzymatic deficiency can be treated with an enzyme to increase the amount of the deficient enzyme in the subject. For example, enzyme replacement therapy (ERT) with a recombinant enzyme, such as imiglucerase (Cerezyme®), velaglucerase alfa (VPRI®) or taliglucerase alfa (Elelyso®), can be used as a second therapeutic agent to treat Type I Gaucher disease. Small molecules that inhibit glycosylceramide synthase, for example, miglustat and eliglustat, can also be used to treat Type I Gaucher disease. A small molecule that acts as a chaperone to stabilize a defective enzyme produced by the subject or a small molecule that reduces the amount of one or more substrates that would normally be processed by an enzyme in the subject can also be used.

One or more therapeutic agents that reduce the symptoms of a LSD can also be administered. For example, an anti-epileptic such as gabapentin or lamotrigine can be used to prevent seizures in a subject. Antibiotics can be used to treat bacterial infections such as pneumonia. Other agents include, but are not limited to, anti-inflammatory agents (e.g., NSAIDs and anti-inflammatory steroids), and muscle relaxants. Dialysis, physical therapy and surgery are also contemplated herein as therapies to treat a LSD.

In some methods for treating or preventing a LSD, the second therapeutic agent can be a tyrosine kinase inhibitor (e.g., nilotinib, bosutinib, imatinib, pazopanib, etc.). Therefore, in some examples, a tyrosine kinase inhibitor and a compound of Formula I, Formula II or Formula III are administered to the subject. In the methods where a tyrosine kinase is administered as a second therapeutic agent, the tyrosine kinase can be a tyrosine kinase inhibitor that differs in selectivity for one or more receptor tyrosine kinases as compared to the compound of Formula I, Formula II or Formula III.

Methods for Treating a Neurodevelopmental Disorder

Also provided are methods for treating a neurodevelopmental disorder in a subject. The methods comprise administering to the subject with the neurodevelopmental disorder an effective amount of a compound having Formula I:

Formula I

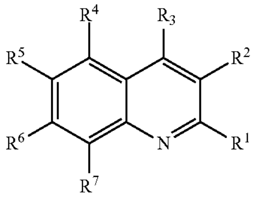

or an isomer or pharmaceutically acceptable salt thereof, wherein $R^1$ is H, $NR^8R^9$, $CR^8R^9R^{10}$, or $OR^8$;

$R^8$, $R^9$ and $R^{10}$ are each independently H, OH, substituted or unsubstituted aryl (e.g., substituted or unsubstituted phenyl), or substituted or unsubstituted alkyl, cycloalkyl, heteroalkyl, cycloheteroalkyl, or heteroaryl.

$R^2$, $R^4$, $R^5$, $R^6$, and $R^7$ are each independently H, OH, halogen, $C_{1-6}$ alkyl, or $C_{1-6}$ alkoxy;

$R^3$ is $NR^{11}R^{12}$ or $OR^{11}$, wherein $R^{11}$ and $R^{12}$ are each independently H, OH, substituted or unsubstituted aryl (e.g., substituted or unsubstituted phenyl), or substituted or unsubstituted alkyl alkyl, cycloalkyl, heteroalkyl, cycloheteroalkyl, or heteroaryl.

In some methods, $R^6$ is halogen (e.g., F, Cl, Br, or I). In some examples, $R^2$, $R^4$, $R^5$, and $R^7$ are each independently not halogen.

In some methods, $R^8$ and $R^9$ are each independently H, OH, $C_1$-$C_3$ alkyl ester optionally substituted with benzyl, or substituted or unsubstituted phenyl.

In some methods, $R^{11}$ and $R^{12}$ are each independently $C_1$-$C_3$ alkyl ester optionally substituted with benzyl, phenyl, or phenyl substituted with $C_1$-$C_6$ alkyl or $C_1$-$C_6$ alkoxy.

In some methods, $R^3$ is $NHR^{11}$, wherein $R^{11}$ is phenyl substituted with methyl as shown below:

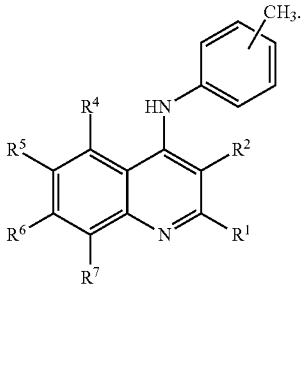

In some methods, $R^3$ is $NHR^{11}$ where $R^{11}$ is phenyl substituted with methoxy as shown below:

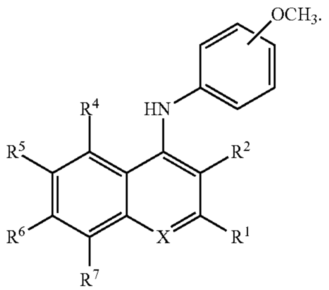

In some methods, $R^3$ is $OR^{11}$ wherein $R^{11}$ is phenyl substituted with methyl as shown below:

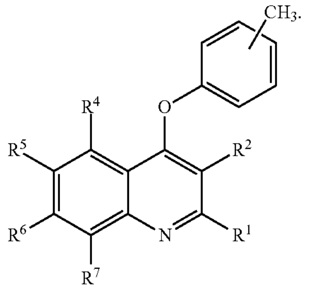

Examples of Formula I include the following compounds:

Compound 1

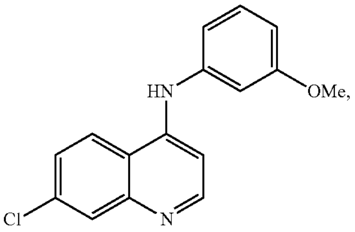

(BK5018)

Compound 2

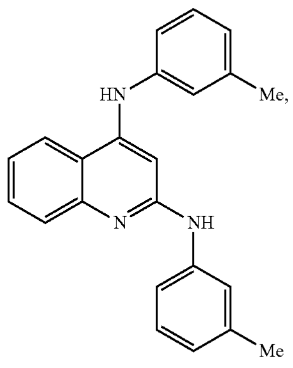

(BK5026)

-continued

Compound 3

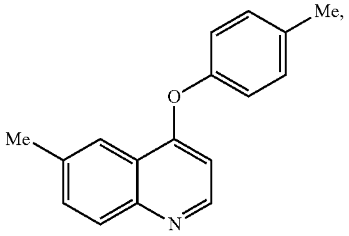

(BK5029)

Compound 4

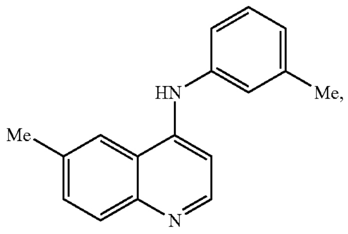

and (BK5030)

Compound 5

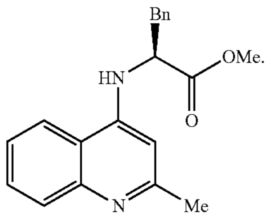

(DH016)

Some methods comprise administering to the subject with the neurodevelopmental disorder an effective amount of a compound having Formula II:

Formula II

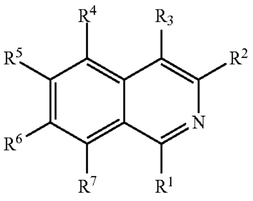

or an isomer or pharmaceutically acceptable salt thereof.

wherein $R^1$ is $NR^8R^9$, $CR^8R^9R^{10}$, or $OR^8$;

$R^8$, $R^9$ and $R^{10}$ are each independently H or substituted or unsubstituted aryl (e.g., substituted or unsubstituted phenyl); In some examples, $R^8$, $R^9$ and $R^{10}$ are each independently H phenyl, or phenyl substituted with $C_1$-$C_6$ alkyl or $C_1$-$C_6$ alkoxy;

$R^2$, $R^3$, $R^4$, $R^6$, and $R^7$ are each independently H, OH, $C_{1-6}$ alkyl, or $C_{1-6}$ alkoxy;

$R^5$ is $NR^{11}R^{12}$ or $OR^{10}$; and $R^{11}$ and $R^{12}$ are each independently H, OH, substituted or unsubstituted alkyl, or substituted or unsubstituted aryl.

In some methods, $R^8$, $R^9$ and $R^{10}$ are each independently H phenyl, or phenyl substituted with $C_1$-$C_6$ alkyl or $C_1$-$C_6$ alkoxy.

In some methods, $R^{11}$ and $R^{12}$ are each independently H, OH, phenyl, or phenyl substituted with $C_1$-$C_6$ alkyl or $C_1$-$C_6$ alkyoxy.

An example of Formula II includes the following compound:

Compound 6

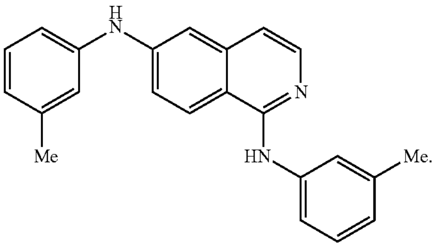

(CL2-296)

Other methods comprise administering to the subject with the neurodevelopmental disorder an effective amount of a compound having Formula III:

Formula III

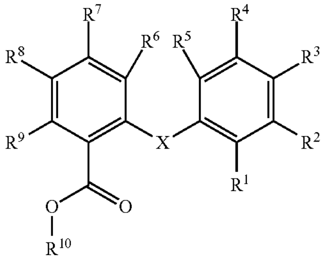

or an isomer or pharmaceutically acceptable salt thereof, wherein

X is $NR^{11}$, S, or O;

$R^{11}$ is H, substituted or unsubstituted alkyl, or substituted or unsubstituted aryl;

$R^1$ is H or $C_1$-$C_6$ alkyl;

$R^2$ is H, OH, halogen (e.g., F, Cl, Br, or I), or $C_1$-$C_6$ alkyl;

$R^3$, $R^4$, $R^5$, $R^6$, $R^7$, $R^8$, and $R^9$ are each independently H, OH, $C_{1-6}$alkyl, or $C_{1-6}$ alkoxy; and $R^{10}$ is —H or $C_{1-6}$ alkyl.

Examples of Formula III include the following compounds:

Compound 7

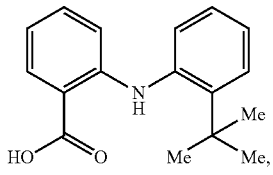

(CL2-287-1)

-continued

Compound 8

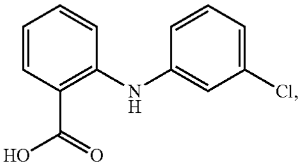

(CL2-287-2)

or an isomer or pharmaceutically acceptable salt thereof.

Some methods comprise administering to the subject with the neurodevelopmental disorder an effective amount of a compound having Formula IV:

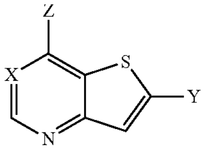

or an isomer or pharmaceutically acceptable salt thereof. In Formula IV, X is N or CH.

Also, in Formula IV, Y is $C_{6-10}$ aryl unsubstituted or substituted with $R^1$; or $C_{5-10}$ heteroaryl unsubstituted or substituted with $R^1$, or N-methylpiperazinyl.

Also, in Formula IV, $R^1$ is $-(CH_2)_n-R^2$, $-(CH_2)_n-C(O)-R^2$, or $-O(CH_2)_n-R^2$.

Additionally, in Formula IV, $R^2$ is —H, —CN, halogen, $C_{1-3}$ alkyl, $C_{1-3}$ alkoxy, phenyl, pyridinyl, amino, $C_{1-3}$ alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkylamino, pyrrolidinyl, hydroxyl pyrrolidinyl, hydroxyl $C_{1-3}$ alkylpyrolidinyl, carboxypyrolidinyl, piperidinyl, $C_{1-3}$ alkylpiperidinyl, di $C_{1-3}$ alkyl piperidinyl, piperazinyl, $C_{1-3}$ alkylpiperazinyl, $C_{1-4}$ alkoxycarbonylpiperazinyl, or morpholinyl; Z is heteroaryl, heterocyclyl, or $NR^3R^4$.

Also, in Formula IV, $R^3$ and $R^4$ are independently selected from H, $C_{1-3}$ alkyl, $C_{1-3}$ alkoxy, or unsubstituted phenyl, and n is an integer selected from 0 to 3.

In some examples of Formula IV, Y is benzyl substituted with $R^1$:

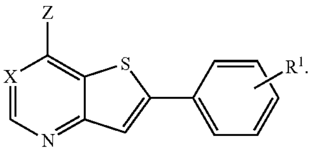

In some examples of Formula IV, Y is benzyl substituted with $R^1$ in the meta position:

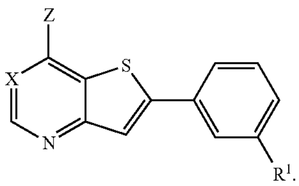

In some examples of Formula IV, Z is $NR^3R^4$, $R^3$ is benzyl or H, $R^4$ is benzyl or H, and Y is benzyl substituted with $R^1$:

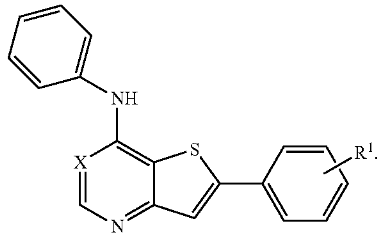

In some examples of Formula IV, Z is $NR^3R^4$, $R^3$ is benzyl or H, $R^4$ is benzyl or H, and Y is benzyl substituted with $R^1$ in the meta position:

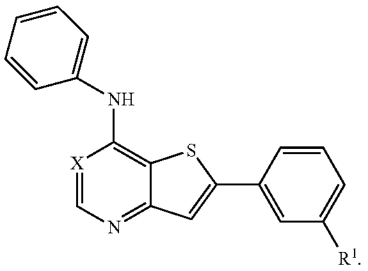

In some examples of Formula IV Z is morpholinyl and Y is benzyl substituted with $R^1$:

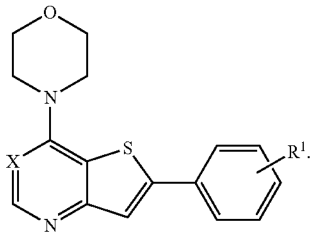

In some examples of Formula IV, Z is morpholinyl and Y is benzyl substituted with $R^1$ in the meta position:

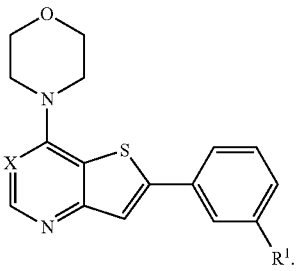

A compound of Formula IV is Compound 9 (BK40197):

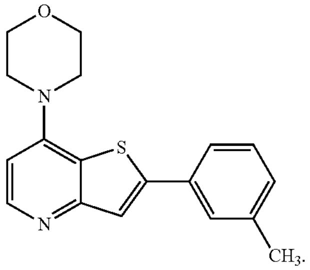

4-(2-(m-tolyl)thieno[3,2-b]pyridin-7-yl)morpholine

Another compound of Formula IV is Compound 10 (BK40193):

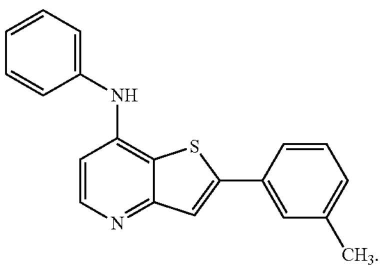

N-phenyl-2-(m-tolyl)thieno[3,2-b]pyridin-7-amine

In some examples of Formula IV, the compound does not comprise one or more halogen atoms. In some examples of Formula IV, Y is 2-n-toluyl. In some examples of Formula IV, Z is heterocyclyl. In some examples of Formula IV, Z is morpholin-1-yl. In some examples of Formula IV, $R^3$ is H and $R^4$ is unsubstituted phenyl.

Optionally, the compound of Formula L Formula, Formula III, or Formula IV inhibits one or more receptor tyrosine kinases selected from the group consisting of Abl, PDGFRα, PDGFRβ, DDR 1, DDR2, cKIT, arginase U, Src, Fyn, VEGFR and Zac. In some examples, the compound of Formula I selectively inhibits Abl, PDGFRα, PDGFRβ, DDR 1, DDR2, cKIT, arginase H, Src, Fyn or VEGR or Zac. In some examples, the compound having Formula I inhibits DDR 1 and/or DDR2. For example, and not to be limiting, Compound 1, Compound 2 Compound 3, Compound 4, Compound 5, Compound 6, Compound 7, Compound 8, Compound 9 or Compound 10, can be used to inhibit DDR1 and/or DDR2. In another example, the compound having Formula I, Formula II, Formula III or Formula IV for example, Compound 1, Compound 2 Compound 3, Compound 4, Compound 5, Compound 6, Compound 7 or Compound 8, Compound 9, or Compound 10, selectively inhibits DDR 1 or DDR2.

During the developmental period, from infancy through adolescence, neurodevelopment and behavior are intricately related. The terms neurodevelopmental and neurobehavioral disorders are used interchangeably to describe a group of disorders with certain basic characteristics that can overlap between different disorders. These include, but are not limited to, agitation, irritability, hyperactivity, cognitive difficulties, memory issues, and difficulties with the activities of daily living. Neurodevelopmental disorders have their onset during the developmental period and persist over a person's lifespan. Examples of neurodevelopmental disorders include, but are not limited to, intellectual developmental disorder, communication disorders affecting speech and language, autism spectrum disorder (ASD), attention deficit hyperactivity disorder (ADHD), and developmental learning disorders. Adult hyperactivity, pediatric hyperactivity, anxiety, agitation and/or irritability are often associated with one or more neurodevelopmental disorders. Therefore, in some methods, the compounds disclosed herein can be used to treat or prevent adult hyperactivity, pediatric hyperactivity, agitation and/or irritability are often associated with a neurodevelopmental disorders.

Neurodevelopmental disorders that can be treated using the methods provided herein include, but are not limited to, ADHD, ASD (for example, autism), specific learning disorder, intellectual disability, a genetic disorder, dyslexia, disgraphia, dyscalculia, expression disorder, comprehension disorder, and a speech disorder (dislalia). Examples of autism include, but are not limited to, autistic disorder, pervasive developmental disorder-not otherwise specified (PDD-NOS), Asperger syndrome, Childhood Disintegrative Disorder or Rett Syndrome.

The methods provided herein optionally include selecting a subject with a neurodevelopmental disorder. One of skill in the art knows how to diagnose a subject with a neurodevelopmental disorder. For example, one or more of the following tests can be used: a genetic test (e.g., identification of a mutation associated with a neurodevelopmental disorder) or familial analysis (e.g., family history, genetic testing of parents), central nervous system imaging (e.g., magnetic resonance imaging, computerized tomography and positron emission tomography), clinical or behavioral tests (e.g., assessments to identify mood disorders, aggressiveness and/or cognitive abnormalities), or laboratory tests (e.g. blood and/or urine tests to identify abnormal levels of metabolites or enzymatic deficiencies).

The methods provided herein optionally further include administering an effective amount of one or more therapeutic agents that reduce the symptoms of a neurodevelopmental disorder. The one or more therapeutic agents can be administered to the subject prior to, simultaneously with, or subsequent to administration of the compound of Formula I, Formula II, Formula III or Formula IV. The one or more therapeutic agents are selected from the group consisting of risperidone, aripiprazole, clozapine, haloperidol, sertraline, secretin, methylphenidate, venlaxafine, fluoxetine, citalopram, bumetanide, memantine, rivastigmine, mirtazapine, melatonin, atomoxetine, DMXB-A, a V1A vasopression receptor antagonist (for example, RG7314), acamprosate, valproic acid, alprazolam, naltrexone and clonazepam.

In some methods for treating a neurodevelopmental disorder, the one or more therapeutic agents can comprise a tyrosine kinase inhibitor (e.g., nilotinib, bosutinib, imatinib, pazopanib, etc.). Therefore, in some examples, a tyrosine kinase inhibitor and a compound of Formula I, Formula II, Formula III or Formula IV are administered to the subject. In the methods where a tyrosine kinase is administered as a second therapeutic agent, the tyrosine kinase can be a tyrosine kinase inhibitor that differs in selectivity for one or more receptor tyrosine kinases as compared to the compound of Formula I, Formula II, Formula III or Formula IV.

Also provided herein is a method for treating cancer comprising administering to a subject with cancer, an effective amount of a compound of Formula I, Formula II, Formula III or Formula IV. Treatment of cancer includes, but is not limited to, reducing tumor size, reducing tumor rate of growth, delaying progression of cancer, and preventing a recurrence of cancer.

As used herein, cancer is a disease characterized by the rapid and uncontrolled growth of aberrant cells. Cancer cells can spread locally or through the bloodstream and lymphatic system to other parts of the body. The cancer can be a solid tumor. In some embodiments, the cancer is a blood or hematological cancer, such as a leukemia (e.g., acute leukemia; acute lymphocytic leukemia; acute myelocytic leukemias, such as myeloblastic, promyelocytic, myelomonocytic, monocytic, erythroleukemia leukemias and myelodysplastic syndrome; chronic myelocytic (granulocytic) leukemia: chronic lymphocytic leukemia; hairy cell leukemia), polycythemia vera, or lymphomas (e.g., Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+anaplastic large-cell lymphoma (ALCL), acute myeloid lymphoma (AML))), multiple myelomas (e.g., smoldering multiple myeloma, non-secretory myeloma, osteosclerotic myeloma, plasma cell leukemia, solitary plasmacytoma and extramedullary plasmacytoma). Waldenstrom's macroglobulinemia, monoclonal gammopathy of undetermined significance, benign monoclonal gammopathy and heavy chain disease. Solid tumors include, by way of example, bone and connective tissue sarcomas (e.g., bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma), brain tumors (e.g., glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma), breast cancer (e.g., adenocarcinoma, lobular (small cell) carcinoma, intraductal carcinoma, medullary breast cancer, mucinous breast cancer, tubular breast cancer, papillary breast cancer, Paget's disease, and inflammatory breast cancer), adrenal cancer (e.g., pheochromocytoma and adrenocortical carcinoma), thyroid cancer (e.g., papillary or follicular thyroid cancer, medullary thyroid cancer and anaplastic thyroid cancer), pancreatic cancer (e.g., insulinoma, gastrinoma, glucagonoma, vipoma, somatostatin-secreting tumor, and carcinoid or islet cell tumor), pituitary cancers (e.g., Cushing's disease, prolactin-secreting tumor, acromegaly, and diabetes insipidus), eye cancers (e.g., ocular melanoma such as iris melanoma, choroidal melanoma, and ciliary body melanoma, and retinoblastoma), vaginal cancers (e.g., squamous cell carcinoma, adenocarcinoma, and melanoma), vulvar cancer (e.g., squamous cell carcinoma, melanoma, adenocarcinoma, basal cell carcinoma, sarcoma, and Paget's disease), cervical cancers (e.g., squamous cell carcinoma and adenocarcinoma), uterine cancers (e.g., endometrial carcinoma and uterine sarcoma), ovarian cancers (e.g., ovarian epithelial carcinoma, borderline tumor, germ cell tumor, and stromal tumor), esophageal cancers (e.g., squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma), stomach cancers (e.g., adenocarcinoma, fungating (polypoid), ulcerating, superficial spreading, diffusely spreading, malignant lymphoma, liposarcoma, fibrosarcoma, and carcinosarcoma), colon cancers, rectal cancers, liver cancers (e.g., hepatocellular carcinoma and hepatoblastoma), gallbladder cancers (e.g., adenocarcinoma), cholangiocarcinomas (papillary, nodular, and diffuse), lung cancers (e.g., non-small cell lung cancer, squamous cell carcinoma (epidermoid carcinoma), adenocarcinoma, large-cell carcinoma and small-cell lung cancer), testicular cancers (e.g., germinal tumor, seminoma, anaplastic, classic (typical), spermatocytic, nonseminoma, embryonal carcinoma, teratoma carcinoma, choriocarcinoma (yolk-sac tumor)), prostate cancers (e.g., adenocarcinoma, leiomyosarcoma, and rhabdomyosarcoma), penile cancers, oral cancers (e.g., squamous cell carcinoma), basal cancers, salivary gland cancers (e.g., adenocarcinoma, mucoepidermoid carcinoma, and adenoidcystic carcinoma), esopharyngeal cancers (e.g., squamous cell cancer and verrucous cancer), skin cancers (e.g., basal cell carcinoma, squamous cell carcinoma and melanoma, superficial spreading melanoma, nodular melanoma, lentigo malignant melanoma, acral lentiginous melanoma), kidney cancers (e.g., renal cell cancer, adenocarcinoma, hypernephroma, fibrosarcoma, transitional cell cancer (renal pelvis and/or ureter), Wilms' tumor), bladder cancers (e.g., transitional cell carcinoma, squamous cell cancer, adenocarcinoma, and carcinosarcoma). In addition, cancers include myxosarcoma, osteogenic sarcoma, endotheliosarcoma, lymphangio endothelio sarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

Any of the methods for treating cancer can further comprise administering a second therapeutic agent to the subject. The second therapeutic agent or therapy can be administered to the subject prior to, simultaneously with, or subsequent to administration of the compound having Formula I, II, III, or IV. Any of the methods provided herein can further comprise chemotherapy, radiation therapy or surgery.

Pharmaceutical Compositions

The term effective amount, as used throughout, is defined as any amount necessary to produce a desired physiologic response, for example, reducing one or more symptoms of a disease (for example, a neurodegenerative disease, a neurodevelopmental disease, a lysosomal storage order disease or a myodegenerative disease), inhibiting or preventing toxic protein aggregation in a neuron, or promoting lysosomal clearance.

Exemplary dosage amounts for administration of any compound described herein, for example, a compound of Formula I, Formula II, Formula III or Formula IV include doses from about 0.5 to about 200 mg/kg of body weight of active compound per day, which may be administered in a single dose or in the form of individual divided doses, such as from 1 to 4 times per day. Alternatively, the dosage amount can be from about 0.01 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 50 mg/kg of body weight of active compound per day, about 1 to about 40 mg/kg of body weight of active compound per day, about 1 to about 30 mg/kg of body weight of active compound per day, about 1 to about 30 mg/kg of body weight of active compound per day, about 1 to about 20 mg/kg of body weight of active compound per day, about 1 to about 10 mg/kg of body weight of active compound per day, about 1 to about 5 mg/kg of body weight of active compound per day, about 30 mg/kg of body weight of active compound per day, about 20 mg/kg of body weight of active compound per day, about 10 mg/kg of body weight of active compound per day, or about 5 mg/kg of body weight of active compound per day.

Optionally, the dosage is less than about 25 mg/kg and can be less than about 24.5, 24 23.5, 23, 22.5, 22, 21.5, 21, 20.5, 20, 19.5, 19, 18.5, 18, 17.5, 17, 16.5, 16, 15.5, 15, 14.5, 14, 13.5, 13, 12.5, 12, 11.5, 11, 10.5, 10, 9.5, 9, 8.5, 8, 7.5, 7, 6.5, 6, 5.5, 5, 4.5, 4, 3.5, 3, 2.5, 2, 1.5, 1, 0.5 mg/kg or any dosage in between these amounts. Optionally, the dosage is less than about 10 mg/kg and can be less than about 9.5, 9, 8.5, 8, 7.5, 7, 6.5, 6, 5.5, 5, 4.5, 4, 3.5, 3, 2.5, 2, 1.5, 1.25, 1.0, 0.9, 0.8, 0.7, 0.6, 0.5, 0.4, 0.3, 0.2, 0.1 mg/kg or any dosage in between these amounts. The dosage can range from about 0.1 mg/kg to about 10 mg/kg, from about 0.1 mg/kg to about 9 mg/kg, from about 0.1 mg/kg to about 8 mg/kg, from about 0.1 mg/kg to about 7 mg/kg, from about 0.1 mg/kg to about 6 mg/kg, from about 0.1 mg/kg to about 5 mg/kg, from about 0.1 mg/kg to about 4 mg/kg, from about 0.1 mg/kg to about 3 mg/kg, from about 0.1 mg/kg to about 2 mg/kg, from about 0.1 mg/kg to about 1 mg/kg, or from about 0.1 mg/kg to about 0.5 mg/kg. One of skill in the art would adjust the dosage as described below based on specific characteristics of the inhibitor and the subject receiving it.

The composition can comprise a single unit dose of a compound of Formula I, Formula II, Formula III or Formula IV, for example, a single unit dose of about 50 mg/kg or less, 40 mg/kg or less, 30 mg/kg or less, 20 mg/kg or less, 10 mg/kg or less, of about 5 mg/kg or less, of about 2.5 mg/kg or less or about 1.5 mg/kg or less of Compound 1 or Compound 2, or a pharmaceutically acceptable salt thereof. Packages including one or multiple, single unit doses of a compound having Formula I, Formula II, Formula III or Formula IV, for example, multiple, single unit doses of Compound 1, Compound 2. Compound 3, Compound 4, Compound 5, Compound 6, Compound 7 and Compound 8, Compound 9 and Compound 10 are also provided. The package can further comprise single or multiple unit doses of one or more second therapeutic agents described herein.

Effective amounts and schedules for administering one or more of the compounds having Formula I, Formula II, Formula III or Formula IV described herein can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, unwanted cell death, and the like. Generally, the dosage will vary with the type of inhibitor, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary and can be administered in one or more dose administrations daily.

The compounds having Formula I, Formula II, Formula III or Formula IV, and other agents described herein can be provided in a pharmaceutical composition. These include, for example, a pharmaceutical composition comprising a therapeutically effective amount of one or more compounds having Formula I and a pharmaceutical carrier. The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy. 22nd edition, Loyd V. Allen et al, editors, Pharmaceutical Press (2012).

Examples of physiologically acceptable carriers include buffers such as phosphate buffers, citrate buffer, and buffers with other organic acids; antioxidants including ascorbic acid, low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, NJ), polyethylene glycol (PEG), and PLURONICS™ (BASF; Florham Park, NJ).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

The compounds described herein can be incorporated into pharmaceutical compositions which allow for immediate release or delivery of those compounds to a mammal. The compounds described herein can also be incorporated into pharmaceutical compositions which allow for modified release, for example, delayed release or extended release (for example, sustained release or controlled release) of those compounds to a mammal for a period of several days, several weeks, or a month or more. Such formulations are described, for example, in U.S. Pat. Nos. 5,968,895 and 6,180,608 and are otherwise known in the art. Any pharmaceutically-acceptable, delayed release or sustained-release formulation known in the art is contemplated.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylfornamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

The compositions are administered in a number of ways depending on whether local or systemic treatment is desired, and on the area to be treated. The compositions are administered via any of several routes of administration, including orally, parenterally, intravenously, intraperitoneally, intracranially, intraspinally, intrathecally, intraventricularly, intramuscularly, subcutaneously, intracavity or transdermally. Pharmaceutical compositions can also be delivered locally to the area in need of treatment, for example by topical application or local injection. Effective doses for any of the administration methods described herein can be extrapolated from dose-response curves derived from in vitro or animal model test systems.

Throughout, treat, treating, and treatment refer to a method of reducing or delaying one or more effects or symptoms of a neurodegenerative disease, a neurodevelopmental disease, a myodegenerative disease, a prion disease, a lysosomal storage disease or cancer. The subject can be diagnosed with a disease or disorder. Treatment can also refer to a method of reducing the underlying pathology rather than just the symptoms. The effect of the administration to the subject can have the effect of, but is not limited to, reducing one or more symptoms of the disease, a reduction in the severity of the disease, the complete ablation of the disease, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As used throughout, by subject is meant an individual. The subject can be an adult subject or a pediatric subject. Pediatric subjects include subjects ranging in age from birth to eighteen years of age. Thus, pediatric subjects of less than about 10 years of age, five years of age, two years of age, one year of age, six months of age, three months of age, one month of age, one week of age or one day of age are also included as subjects. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

Synthesis and Characterization of Compounds

1. General Information

Commercially available m-anisidine, 4-chloroquinolines, 6-bromo-1-chloroisoquinoline, m-toluidine, p-cresol, L-phenylalanine methyl ester, reagents, catalysts and solvents were used as purchased without further purification. NMR spectra were obtained at 400 MHz ($^1$H NMR) and 100 MHz ($^{13}$C NMR) in deuterated solvents. Reaction products were purified by column chromatography on silica gel (particle size 40-63 μm) as described below.

2. Synthetic Methods and Compound Characterization

2.1. Synthesis of Quinoline Derivatives

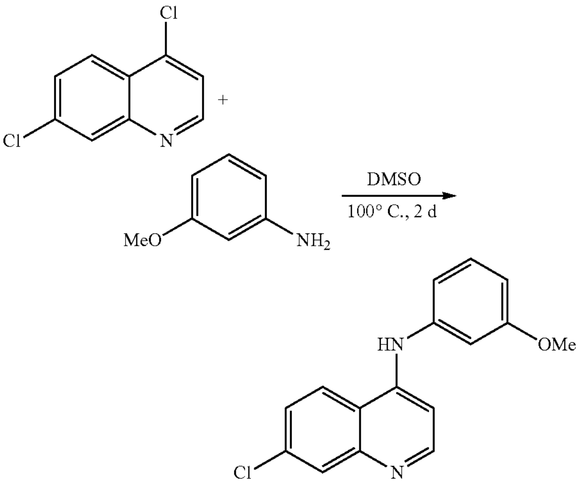

BK5018, 95%

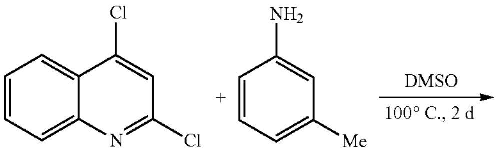

-continued

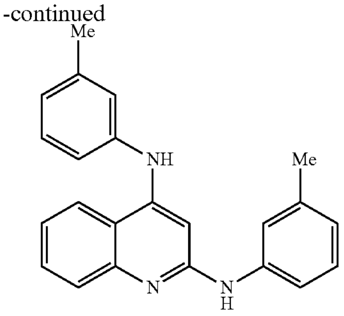

BK5026, 76%

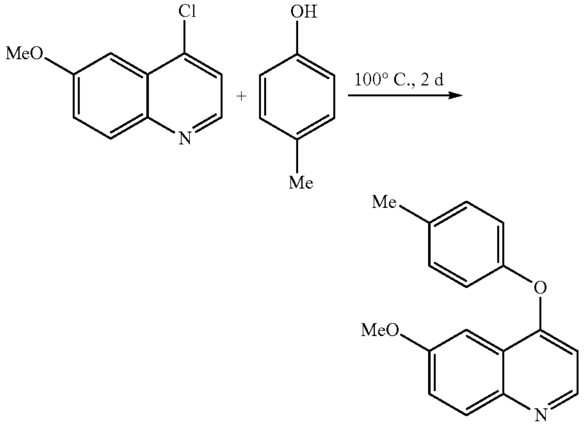

BK5029, 95%

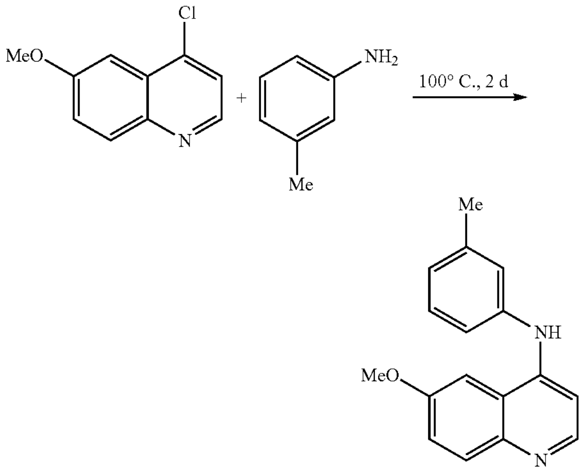

BK5030, 98%

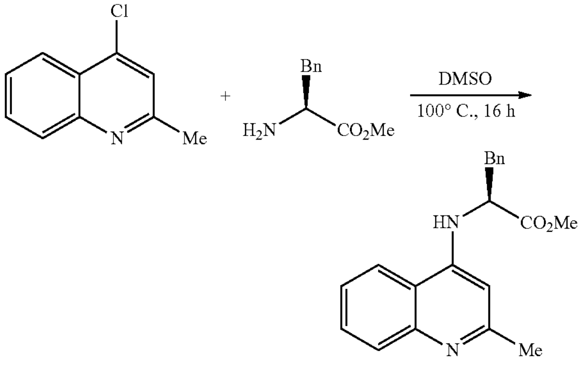

DH016, 34%

General Procedure for the Nucleophilic Aromatic Substitution Reactions

An 8 mL pressure vessel was charged with the quinoline and the amine in DMSO or under solvent free conditions as described below. The pressure vessel was then placed in a 100° C. oil bath and stirred for 16 hours to 2 days. After full conversion was achieved based on $^1$H NMR analysis, the reaction mixture was extracted with EtOAc and washed with water.

The combined organic layers were dried over sodium sulfate and the solvent was removed in vacuo. The crude product was purified by flash chromatography on silica gel as described below.

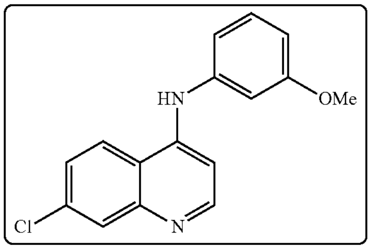 [SMILES: COc1cccc(Nc2ccnc3cc(Cl)ccc23)c1]

7-Chloro-N-(3-methoxyphenyl)quinolin-4-amine (BK5018)

Compound BK5%18 was obtained as a colorless solid in 95% yield (135 mg, 0.475 mmol) from 4,7-dichloroquinoline (98 mg, 0.5 mmol) and 3-methoxyaniline (154 mg, 1.25 mmol) in 1 mL of DMSO after 2 days at 100° C. by following the general procedure described above. The crude product was purified using flash chromatography on silica gel using hexanes/EtOAc (1:1). $R_f$=0.2 (hexanes/EtOAc, 1:1); $^1$H NMR (400 MHz, Chloroform-d) δ=8.56 (d, J=5.3 Hz, 1H), 8.02 (d, J=1.8 Hz, 1H), 7.87 (d, J=8.9 Hz, 1H), 7.44 (dd, J=9.0, 2.2 Hz, 1H), 7.32 (dd, J=8.0, 8.0 Hz, 1H), 7.02 (d, J=5.3 Hz, 1H), 6.93-6.80 (m, 2H), 6.79-6.66 (m, 2H), 3.82 (s, 3H); $^{13}$C NMR (100 MHz, Chloroform-d) δ=161.0, 152.1, 149.8, 147.6, 140.9, 135.5, 130.7, 129.1, 126.3, 121.4, 118.3, 115.0, 110.4, 108.6, 103.1, 55.5.

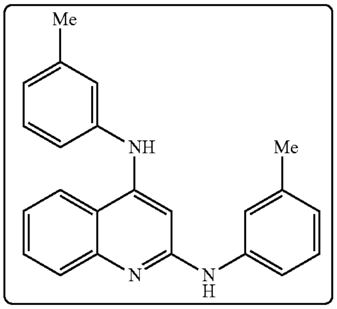 [SMILES: Cc1cccc(Nc2cc(Nc3cccc(C)c3)c3ccccc3n2)c1]

$N^2$,$N^4$-Di-m-tolyquinoline-2,4-diamine (BK5026)

Compound BK5026 was obtained as a colorless solid in 76% yield (129 mg, 0.38 mmol) from 2,4-dichloroquinoline (98 mg, 0.5 mmol) and m-toluidine (133 mg, 1.25 mmol) in 1 mL of DMSO after 2 days at 100° C. by following the general procedure described above. The crude product was purified using flash chromatography on silica gel using DCM/MeOH (9:1). $R_f$=0.3 (DCM/MeOH. 9:1); $^1$H NMR (400 MHz, Chloroform-d) δ=7.80 (d, J=8.2 Hz, 1H), 7.68 (d, J=8.4 Hz, 1H), 7.53 (dd, J=7.7, 7.7 Hz, 1H), 7.29-7.19 (m, 3H), 7.19-7.09 (m, 4H), 7.08-7.01 (m, 2H). 6.93 (d, J=7.5 Hz, 1H), 6.83 (d, J=7.1 Hz, 1H), 6.60 (s, 1H), 2.33 (s, 3H), 2.29 (s, 3H); $^{13}$C NMR (100 MHz, Chloroform-d) δ=155.2, 149.1, 147.2, 139.9, 139.7, 139.1, 130.3, 129.5, 129.0, 126.1, 125.4, 124.1, 123.2, 122.5, 121.5, 120.0, 119.6, 117.9, 116.7, 110.1, 90.4, 21.6, 21.6.

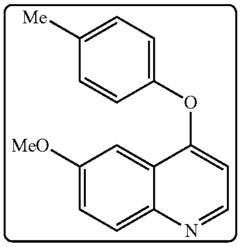 [SMILES: COc1ccc2nccc(Oc3ccc(C)cc3)c2c1]

6-Methoxy-4-(p-tolyloxy)quinoline (BK5029)

Compound BK5029 was obtained as a colorless solid in 95% yield (126 mg, 0.475 mmol) from 4-chloro-6-methoxy-quinoline (97 mg, 0.5 mmol) and p-cresol (I mL) after 2 days at 100° C. by following the general procedure described above. The crude product was purified using flash chromatography on silica gel using hexanes/EtOAc (7:3). $R_f$=0.3 (hexanes/EtOAc, 1:1); $^1$H NMR (400 MHz, Chloroform-d) 6=8.52 (d, J=5.2 Hz, 1H), 7.98 (d, J=9.2 Hz, 1H), 7.60 (d, J=2.9 Hz, 1H), 7.39 (d, J=9.1, 2.9 Hz, 1H), 7.25 (d, J=7.7 Hz, 2H), 7.08 (d, J=8.0 Hz, 2H), 6.51 (d, J=4.8 Hz, 1H), 3.95 (s, 3H), 2.40 (s, 3H); $^{13}$C NMR (100 MHz, Chloroform-d) δ=161.3, 157.7, 152.2, 148.6, 146.0, 135.3, 130.8, 130.8, 122.9, 122.3, 121.0, 104.5, 99.5, 55.7, 21.0.

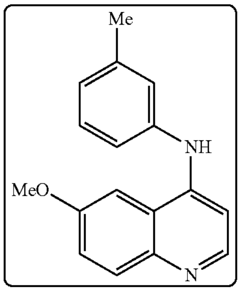 [SMILES: COc1ccc2nccc(Nc3cccc(C)c3)c2c1]

6-Methoxy-N-(m-tolyl)quinolin-4-amine (BK5030)

Compound BK5030 was obtained as a colorless solid in 98% yield (129 mg, 0.49 mmol) from 4-chloro-6-methoxy-quinoline (97 mg. 0.5 nmol) and m-toluidine (I mL) after 2 days at 100° C. by following the general procedure described above. The crude product was purified using flash chromatography on silica gel using hexanes/EtOAc (1:1). $R_f$=0.2 (hexanes/EtOAc, 1:1); $^1$H NMR (399 MHz, DMSO-$d_6$) δ=8.69 (s, 1H), 8.33 (d, J=5.2 Hz, 1H), 7.79 (d, J=9.1 Hz, 1H), 7.72 (d, J=2.7 Hz, 1). 7.38-7.25 (m, 2H), 7.20-7.12 (m, 2H), 6.95 (d, J=7.5 Hz, 1H), 6.91 (d, J=5.2 Hz, 11H), 3.92 (s, 3H), 2.34 (s, 3H); $^{13}$C NMR (100 MHz, DMSO-$d_6$) δ=156.3, 148.1, 146.6, 144.7, 140.6, 138.7, 130.7, 129.1, 124.2, 122.9, 121.0, 120.3, 119.3, 101.8, 100.9, 55.7, 21.0.

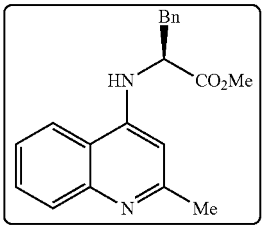 [SMILES: COC(=O)[C@H](Cc1ccccc1)Nc1cc(C)nc2ccccc12]

Methyl (2-methylquinolin-4-yl)-L-phenylalaninate (DH016)

Compound DH016 was obtained from 4-chloroquinaldine (0.1 mL, 0.5 mmol) and L-phenylalanine methyl ester (321.8 mg. 1.5 mmol) in 0.7 mL of DMSO after 16 hours at 100° C. as an oil in 34% yield (54.3 mg, 0.17 mmol) by following the general procedure described above. The crude product was purified using flash chromatography on silica gel using ether/triethylamine (99:1). $R_f$=0.15 (ether/triethylamine, 99:1); $^1$H NMR (400 MHz, Chloroform-d) δ=7.85 (d, J=8.0 Hz, 1H), 7.56 (m, 2H), 7.32 (m, 1H), 7.22 (m, J=4.0 Hz. 3H), 7.07 (m, 2H), 6.19 (s, 1H), 5.38 (d, J=8.0 Hz, 1H), 4.53 (dd, J=4.0 Hz, 1H), 3.70 (s, 3H), 3.27 (dd, J=4.0, 12.0 Hz, 1H), 3.17 (dd, J=4.0, 12.0 Hz, 1H), 2.53 (s, 3H). $^{13}$C NMR (400 MHz, Chloroform-d) δ=172.3, 159.4, 147.5, 135.5, 129.3, 129.1, 128.7, 127.3, 124.3, 119.1, 117.4, 110.0, 99.6, 56.3, 52.5, 37.9, 25.7.

2.2. Synthesis of the Isoquinoline Derivative

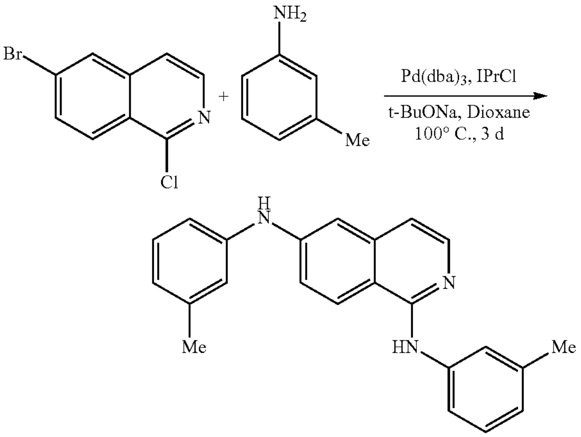

CL2-296, 48% yield $N^4$,$N^6$-Di-m-tolylisoquinoline-1,6-diamine (CL2-296)

An 8 mL vial was charged with 6-bromo-1-chloroisoqui-noline (121.3 mg, 0.5 mmol). $Pd_2(dba)_3$ (9.2 mg, 0.01 mmol), 1,3-bis(2,6-diisopropylphenyl)imidazolium chloride (12.8 mg, 0.03 mmol) and dioxane (1.7 mL). m-Toluidine (321.5 mg, 3.0 mmol) and NaOt-Bu (73.0 mg, 0.75 mmol) were added. The resulting mixture was place in a 100° C. oil bath and stirred for 3 days. The reaction mixture was quenched with $NaHCO_3$ (20 mL) and extracted with EtOAc (3×20 mL). The combined organic layers were dried over sodium sulfate and the solvent was removed in vacuo. The crude product was purified by flash chromatography on silica gel using diethyl ether/hexanes (9:1). Compound CL2-296 was obtained as a colorless solid in 48% yield (81.4 mg, 0.24 mmol). $R_f$=0.20 ($CHCl_3$/MeOH, 9:1); $^1H$ NMR (400 MHz, Chloroform-d): δ=7.87 (d, J=5.8 Hz, 1H), 7.63 (d, J=8.9 Hz, 1H), 7.33-7.27 (m, 2H), 7.20-7.03 (m, 3H), 7.00 (d, J=9.1 Hz, 1H), 6.97-6.68 (m, 6H), 5.96 (s, 1H), 2.25 (s, 3H), 2.24 (s, 3H); $^{13}C$ NMR (100 MHz, Chloroform-d): δ=152.3, 145.1, 141.5, 141.3, 140.7, 139.4, 139.3, 138.7, 129.3, 128.8, 123.7, 123.3, 120.9, 120.7, 118.4, 117.4, 117.0, 113.5, 112.8, 108.6, 21.5, 2.3. Anthranilic Acids

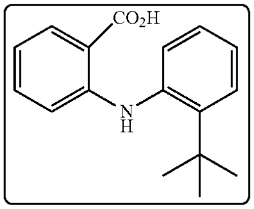 [SMILES: CC(C)(C)c1ccccc1Nc1ccccc1C(=O)O]

2-((2-(tert-Buty)phenyl)amino)benzoic acid (CL2-287-1)

Compound CL2-287-1 was synthesized according to a literature protocol (Wolf et al. *J. Org. Chem.* 72: 3270-3273 (2006)). NMR spectra were in accordance with the reported compound.

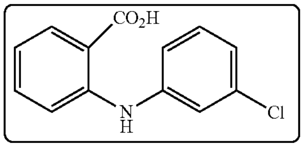 [SMILES: O=C(O)c1ccccc1Nc1cccc(Cl)c1]

2-((3-Chlorophenyl)amino)benzoic acid (CL2-287-2)

Compound CL2-287-2 was synthesized according to a literature protocol (Wolf et al.). NMR spectra were in accordance with the reported compound.

Cell Culture

Rat neuroblastoma B35 cells were grown in Dulbecco's Modified Eagle's Medium (DMEM) with 10% Fetal Bovine Serum (FBS) and 1% penicillin/streptomycin and incubated at 37° C. with 5% $CO_2$. For the experiments, cells were transferred to 12-well plates (Cat. #150628, ThermoFisher, Waltham, MA) and grown to at least 70% confluence. Transient transfection was performed with 3 μg P301L tau (Cat. #30145, Addgene) cDNA or 3 μg human α-synuclein cDNA using Fugene HD transfection reagent (Cat. #E2311, Promega, Madison WI) for 24 hours. Cells were treated with 1 mM, 100 μM, 10 μM, 1 μM, 0.1 μM, 0.01 μM, and 0.001 μM dissolved in DMSO or an equivalent 5 μL of DMSO for 5 hours. Cell culture media was collected and cells were harvested using sodium-tris, EDTA, NP-40 (STEN) buffer and centrifuged at 10,000×g for 20 minutes at 4'C and supernatant was collected. Cell viability was determined via lactate dehydrogenase assay (Cat. #88954, Thermofisher) and MTT assay (Cat. #V13154, Thermofisher). Protein was extracted by removing culture medium and adding 0.2 ml 1×STEN buffer (50 mM Tris (pH 7.6), 150 mM NaCl, 2 mM EDTA, 0.2% NP-40, 0.2% BSA, 20 mM PMSF and protease cocktail inhibitor) to cell layer and incubated on ice for 10 minutes. The bottom of the well was scraped and allowed to incubate on ice for an additional 10 minutes. Cell lysates were collected, stored at −80° C., and used for additional analyses.

Drug Preparation

Compound 1 (BK5018), Compound 2 (BK5026), Compound 3 (BK5029), Compound 4 (BD5040), Compound 6 (CL2-296). Compound 7 (CL-2-287-1) and Compound 8 (CL-2-287-2) with molecular weights of 284, 339.265, 264, 339, 269 and 247 g/mol, respectively, were diluted in Dimethyl Sulfoxide (DMSO) to final concentrations of 100 μM, 10 μM, 1 μM, 0.1 μM, 0.01 μM, and 0.001 μM. Drugs were stored at −80° C.

MTT Assay

To measure cell viability, cells were incubated with 500 μL of Dulbecco's Modified Eagle's Medium (DMEM) containing 50 μL of (3-[4,5-dimethylthiazol-2-yl]-2,5-diphenyltetrazolium bromide (MTT)) for 5 hours at 37° C. and 5% $CO_2$. The media was aspirated so that 125 μL of media remained. The formazan salts were dissolved in 250 μL of DMSO. Absorbance was read against a blank containing 125 μL of media and MTT, and 250 μL of DMSO at 570 nm.

Lactate Dehydrogenase (LDH) Assay

Cellular cytotoxicity was quantitatively measured by assessment of LDH, a cytosolic enzyme that is released from damaged cells into the cellular media, after exposure to the drug 5 hours after initial dosage. The cell culture media was collected, and an aliquot was coupled with a lactate and NAD+. LDH catalyzes the reaction that converts lactate into pyruvate to produce NADH. NADH, in turn, reduces a tetrazolium salt (NT) into a red formazan product. The amount of LDH in the media is proportional to the amount of formazan which was measured at 490 nm. The absorbance at 680 nm, to measure the background signal from the instrument, was subtracted from the absorbance at 490 nm to calculate the LDH activity.

Cell Culture Transfection and Treatment

To perform transient transfection of α-synuclein into the rat neuroblastoma B35 cells FuGene® HD Transfection Reagent (Promega Corporation, Madison, WI) was used. Cells were grown in 12-well dishes. A mixture containing 12 μg of cDNA, 540 μg of DMEM containing 2% FBS, and 60 pd of FuGene® HD Transfection Reagent was incubated for 10 minutes. The cells were treated with 50 μl of the FuGene® HD Transfection Reagent/DNA mixture for 24 hours. Cells were harvested after transfection, media was aspirated, the cells were treated with 200 μl of Sodium Tris EDTA NP40 (STEN) lysis buffer then scraped off the plate and collected into a 1.5 ml centrifuge tube.

Results

Figure 1B:
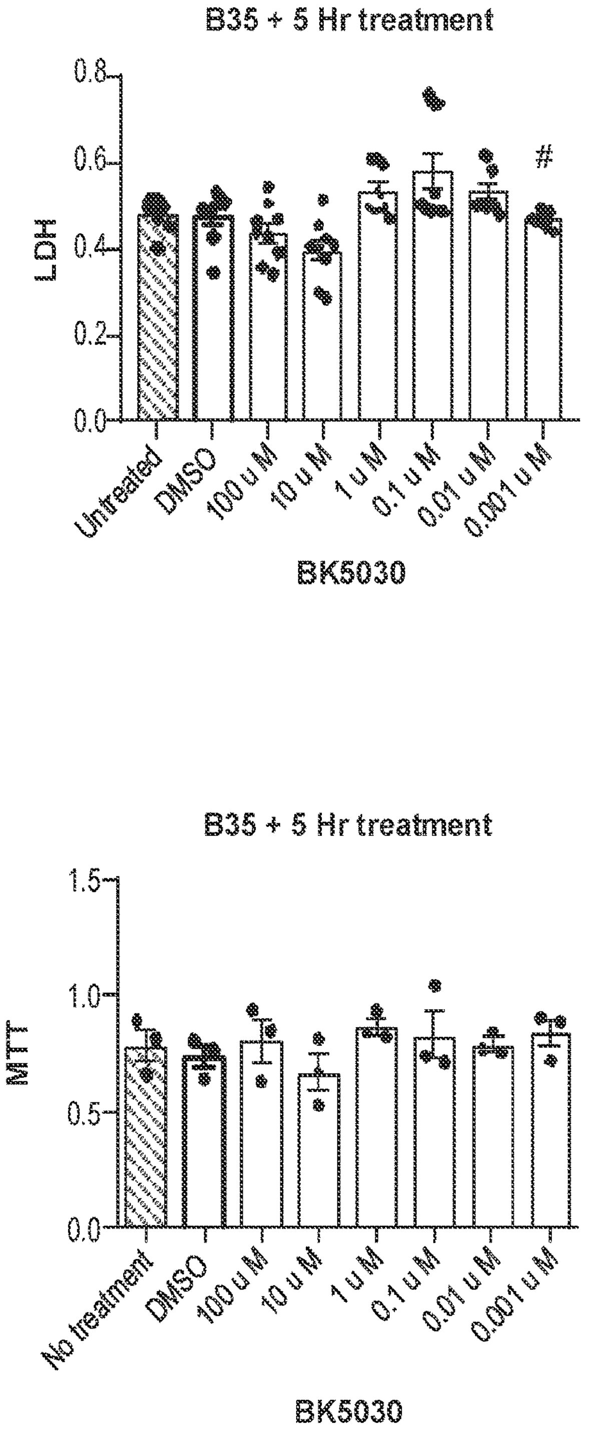
FIG. 1B (top panel) shows that no concentration of BK5030 displayed increased toxicity in B35 rat neuroblastoma cells, as measured by LDH assay.
Figure 1C:
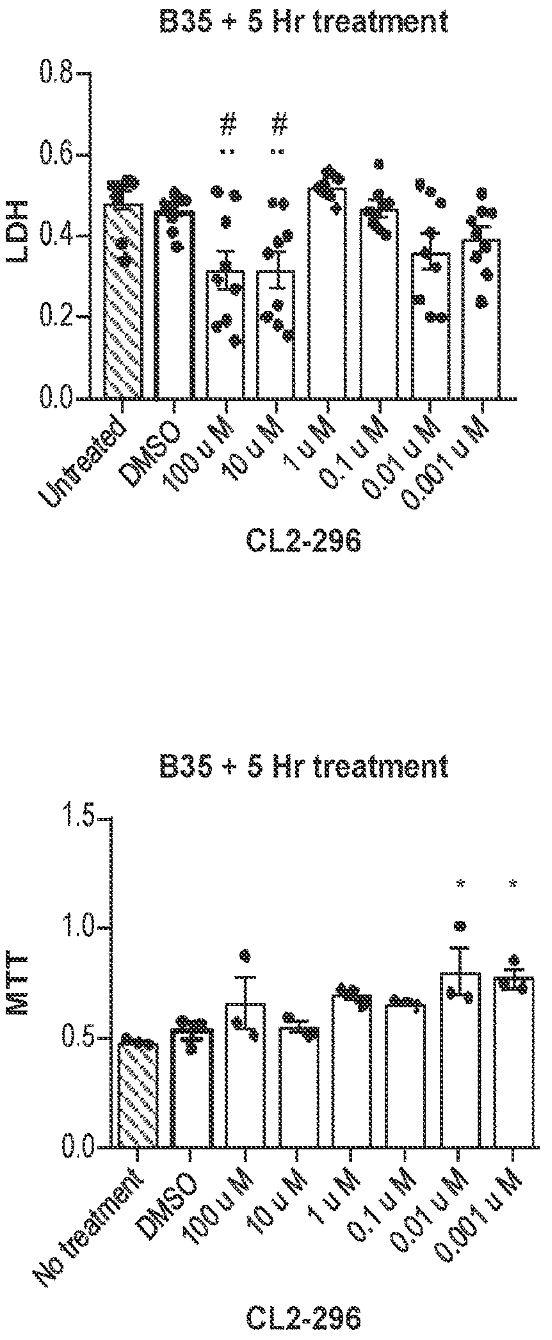
FIG. 1C (top panel) shows that 100 μM and 10 μM concentrations of CL2-296 displayed decreased levels of LDH and no other concentration of CL2-296 displayed increased cell toxicity in B35 rat neuroblastoma cells, as measured by LDH assay.
Figure 1D:
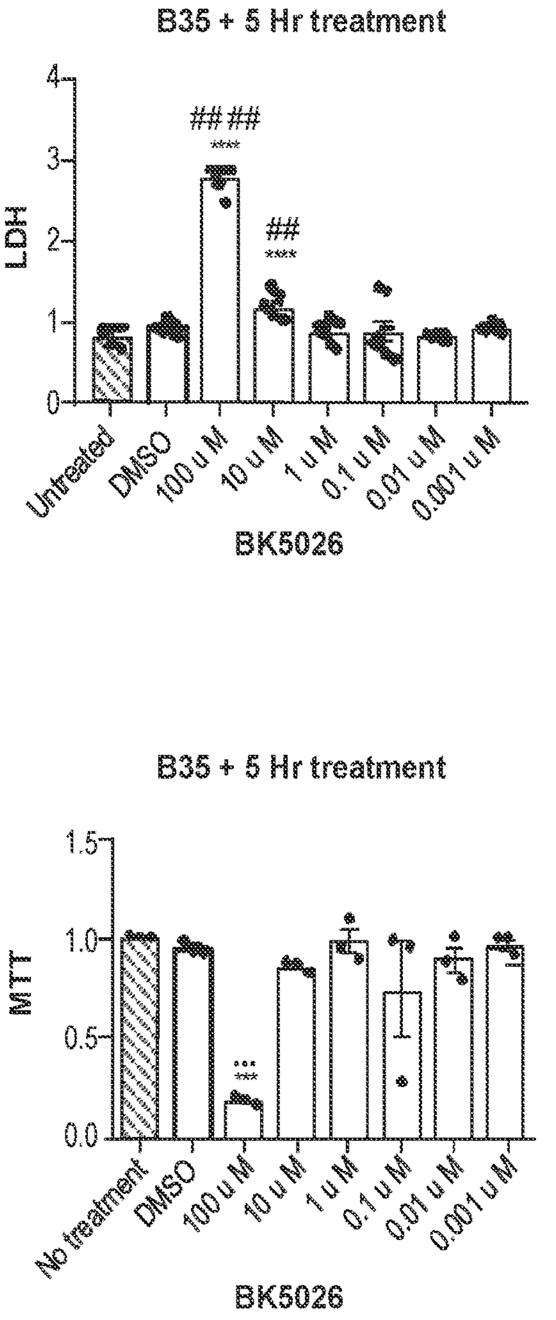
FIG. 1D (top panel) shows that 100 uM and 10 uM concentrations of BK5026 displayed increased levels of cell toxicity, as measured by LDH assay.
Figure 1E:
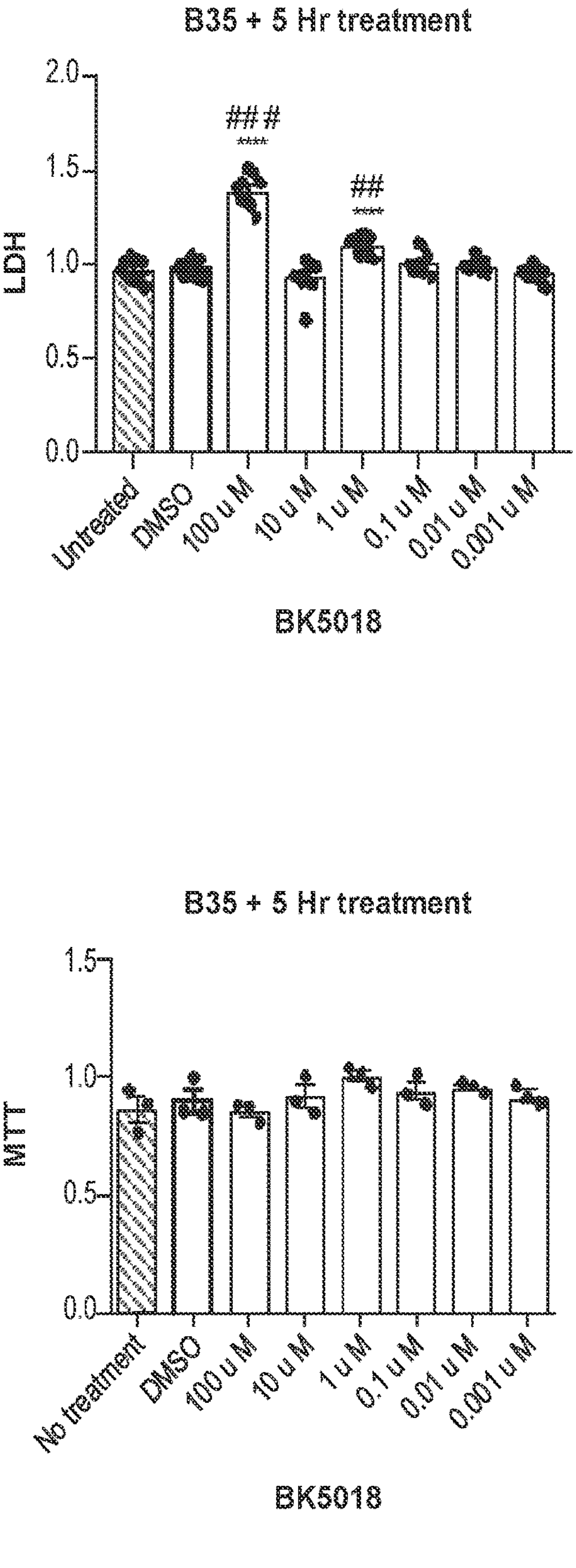
FIG. 1E (top panel) shows that 100 uM and 1 uM of BK5018 displayed increased toxicity, as measured by LDH assay.

Compound 1 (BK5018), Compound 2 (BK5026), Compound 3 (BK5029), Compound 4 (BD5030), Compound 6 (CL2-296), Compound 7 (CL-2-287-1) and Compound 8 (CL-2-287-2) were tested for cell toxicity in B35 rat neuroblastoma via LDH assay. These compounds were also tested for cell viability in MIT assays. As shown in FIG. 1A (top panel) low doses of BK5029 displayed increased toxicity. As shown in FIG. 1B (top panel), no concentration of BK5030 displayed increased toxicity. As shown in FIG. 1C (top panel), 100 μM and 10 μM concentrations of CL2-296 displayed decreased levels of LDH and no other concentration of CL2-296 displayed increased cell toxicity. As shown in FIG. 1D (top panel), 100 μM and 10 μM concentrations of BK5026 displayed increased levels of cell toxicity. As shown in FIG. 1E, 100 μM and 1 μM of BK5018 displayed increased levels of LDH.

Figure 2:
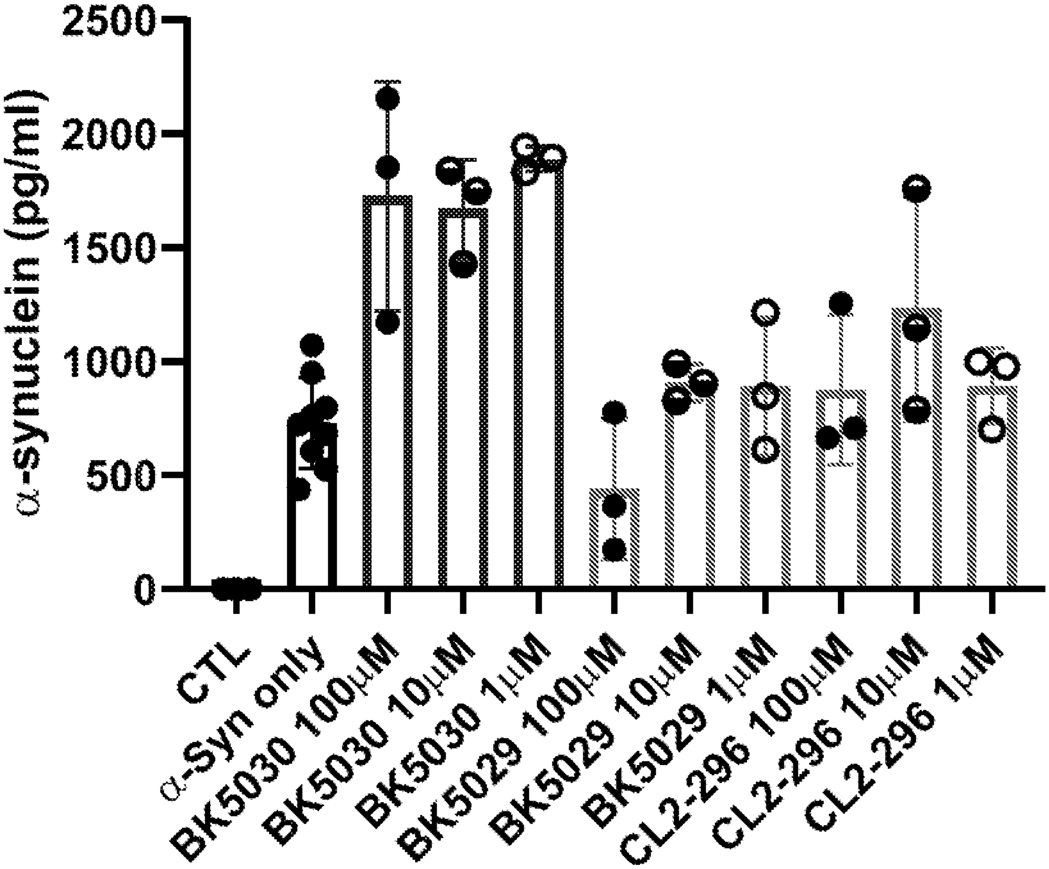
FIG. 2 shows that BK5030, BK5029, and CL2-296 do not significantly reduce the levels alpha-synuclein in α-synuclein-transfected B35 rat neuroblastoma cells.

Compound 3 (BK5029), Compound 4 (BD5030), Compound 6 (CL2-296) were also tested for their ability to reduce alpha-synuclein in α-synuclein-transfected rat neuroblastoma B35 cells. As shown in FIG. 2, after treatment for five hours with 100 μM, 10 μM and 1 μM concentrations of BK5030, BK5029, and CL2-296, none of the compounds significantly reduced the level of alpha-synuclein.

Figure 4:
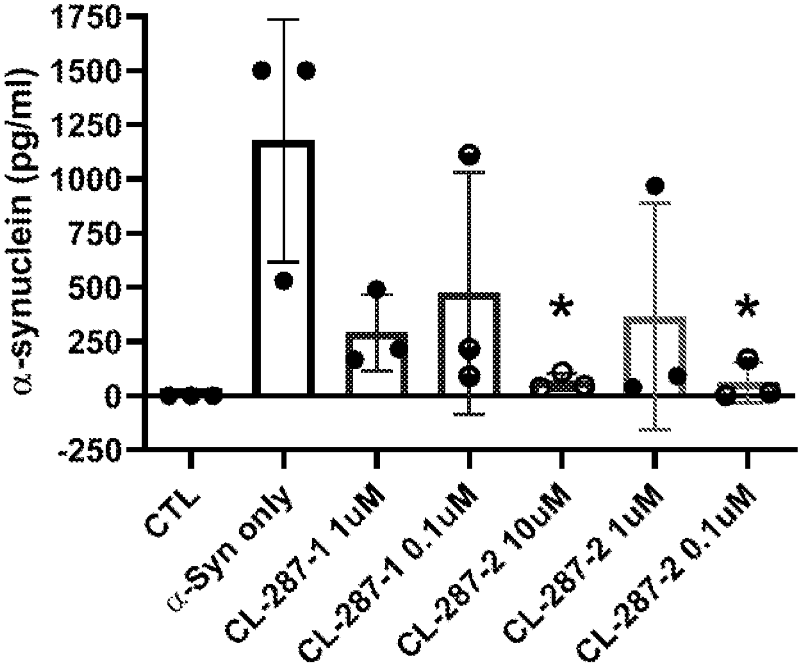
FIG. 4 shows that treatment of cells with 10 μM CL-287-1 and 0.1 μM CL-287-2 significantly reduced the level of α-synuclein in α-synuclein-transfected B35 rat neuroblastoma cells.

As shown in FIGS. 3A and 3B (top panels), treatment of B35 rat neuroblastoma cells with Compound 7 (CL-2-287-1) and Compound 8 (CL-2-287-2) at 100 μM or less did not show increased cell toxicity. Compound 7 (CL-2-287-1) and Compound 8 (CL-2-287-2) were also tested for their ability to reduce alpha-synuclein in α-synuclein-transfected rat neuroblastoma B35 cells. As shown in FIG. 4, treatment of cells with 10 uM CL-287-1 and 0.1 uM CL-287-2 significantly reduced the level of alpha-synuclein in transfected cells.

Example 2

Synthesis and Characterization of Thieno[3,2-b]Pyridine Derivatives

General Information

Commercially available 7-chloro-2-iodothieno[3,2-b] pyridine (1), m-tolylboronic acid (2), aniline (4), m-anisidine (5), morpholine (6), reagents, catalysts and solvents were used as purchased without further purification. NMR spectra were obtained at 400 MHz ($^1$H NMR) and 100 MHz ($^{13}$C NMR) in deuterated solvents. Reaction products were purified by column chromatography on silica gel (particle size 40-63 μm) as described below.

Synthetic Methods and Compound Characterization

Synthesis of thieno[3,2-b]pyridine Compounds 7-10

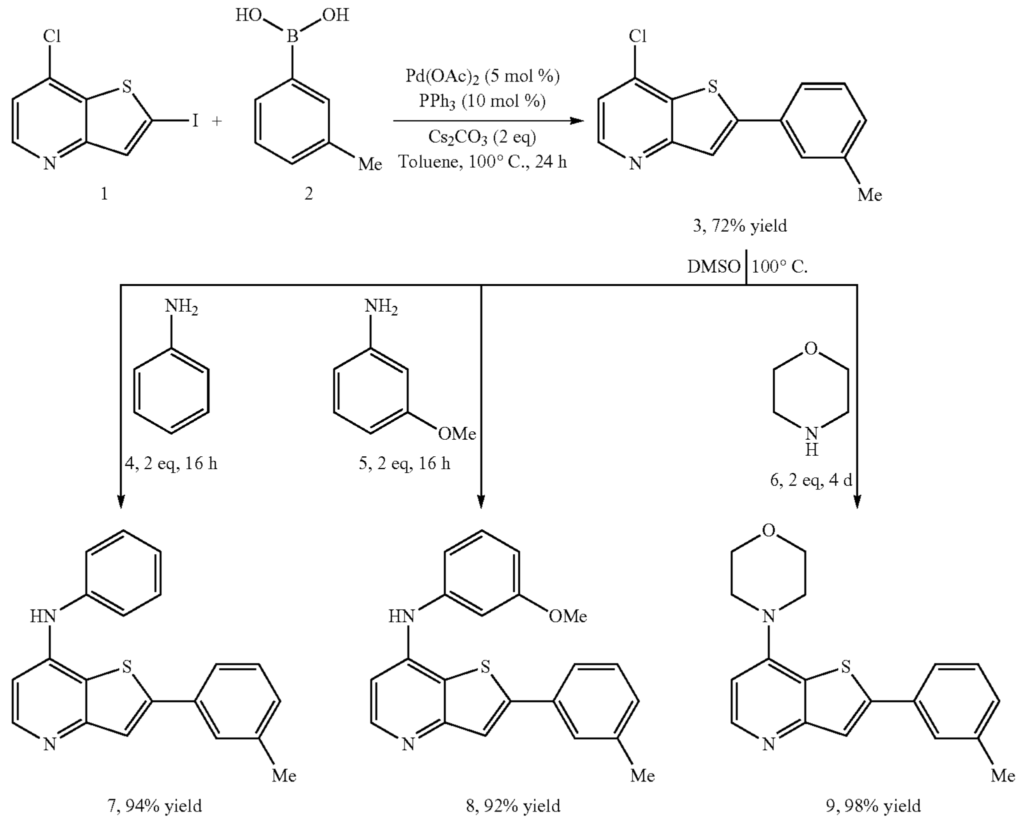

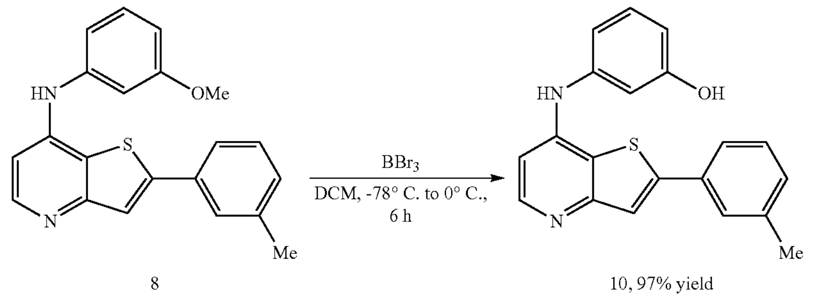

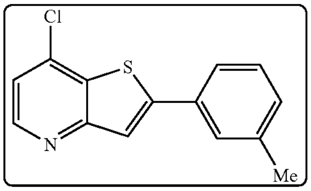 [SMILES: Cc1cccc(-c2cc3nccc(Cl)c3s2)c1]

7-Chloro-2-(m-tolyl)thieno[3,2-b]pyridine (3). A mixture of 7-chloro-2-iodothieno[3,2-b]pyridine (1) (500 mg, 1.69 mmol), 3-methylphenylboronic acid (2) (230 mg, 1.69 mmol), palladium(I) acetate (19 mg, 0.084 mmol), triphenylphosphine (44 mg, 0.169 mmol) and cesium carbonate (1.101 g, 3.38 mmol) in 15 mL of toluene was heated at reflux for 24 h. The reaction mixture was cooled to room temperature and partitioned between water and dichloromethane. The organic layer was washed with saturated aqueous sodium chloride, dried over sodium sulfate, filtered, and concentrated in vacuo. The crude product was purified by flash chromatography on silica gel using hexanes-ethyl acetate (8:2) as mobile phase. Compound 3 was obtained as a colorless solid in 72% yield (315 mg, 1.21 mmol). $R_f$=0.2 (hexanes/EtOAc, 1:1); $^1$H NMR (400 MHz, Chloroform-d) δ=8.54 (d, J=5.1 Hz, 1H), 7.73 (s, 1H), 7.55-7.52 (m, 2H), 7.34 (dd, J=7.8, 7.8 Hz, 1H), 7.23 (m, 1H), 7.21 (d, J=5.1 Hz, 1H), 2.42 (s, 3H); $^{13}$C NMR (100 MHz, Chloroform-d) δ=158.2, 149.6, 148.2, 139.0, 137.6, 133.2, 133.0, 130.4, 129.2, 127.3, 123.8, 120.8, 118.6, 21.5; Anal. Calcd. for $C_{14}H_{10}ClNS$: C, 64.74; H, 3.88; N, 5.39. Found: C, 64.76; H, 4.05; N, 5.28.

General Procedure for the Nucleophilic Aromatic Substitution Reactions

A 5 mL pressure vessel was charged with 7-chloro-2-(n-tolyl)thieno[3,2-b]pyridine (3) (0.3 mmol), the amine (0.6 mmol) and DMSO (1.0 mL). The pressure vessel was then placed in a 100° C. oil bath and stirred for 16 h to 4 days. After full conversion was achieved based on $^1$H NMR analysis, the reaction mixture was extracted with EtOAc and washed with water. The combined organic layers were dried over sodium sulfate and the solvent was removed in vacuo. The crude product was purified by flash chromatography on silica gel using with hexanes-ethyl acetate as mobile phase as described below.

BK-40143

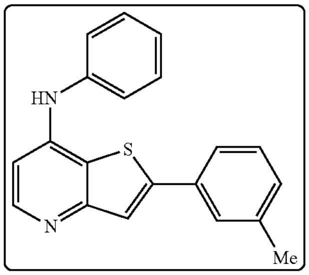

N-Phenyl-2-(m-tolyl)thieno[3,2-b]pyridin-7-amine (7). Compound 7 was obtained as a colorless solid in 94% yield (89 mg, 0.282 mmol) from 7-chloro-2-(n-tolyl)thieno[3,2-b]pyridine (78 mg, 0.3 mmol) and aniline (56 mg. 0.6 nmol) in 1 mL of DMSO after 16 hours at 100° C. by following the general procedure described above. $R_f$=0.2 (hexanes/EtOAc, 1:1); $^1$H NMR (400 MHz, Chloroform-d) δ=8.38 (m, 1H), 7.70 (s, 1H), 7.57-7.50 (m, 2H), 7.43-7.38 (m, 2H), 7.37-7.23 (m, 3H), 7.21-7.17 (m, 2H), 6.90 (m, 1H), 6.15 (s, 1H), 2.43 (s, 3H); $^{13}$C NMR (100 MHz, Chloroform-d) δ=158.5, 148.9, 146.5, 145.9, 139.4, 139.0, 133.7, 129.9, 129.7, 129.6, 129.1, 127.3, 124.8, 123.8, 122.7, 122.5, 121.6, 120.7, 102.6, 21.6: Anal. Calcd. for $C_{20}H_{16}N_2S$: C, 75.92; H, 5.10; N, 8.85. Found: C, 75.71; H, 5.32; N, 9.11.

BK40195

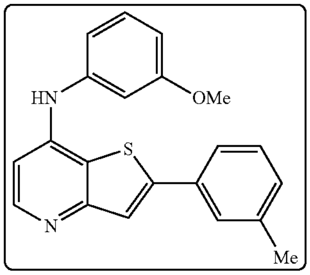

N-(3-Methoxyphenyl)-2-(m-tolyl)thieno[3,2-b]pyridin-7-amine (8). Compound 8 was obtained as a colorless solid in 92% yield (95 mg, 0.276 mmol) from 7-chloro-2-(m-tolyl)thieno[3,2-b]pyridine (78 mg, 0.3 mmol) and m-anisidine (74 mg, 0.6 mmol) in 1 mL of DMSO after 16 hours at 100° C. by following the general procedure described above. $R_f$=0.2 (hexanes/EtOAc, 2:1); $^1$H NMR (400 MHz, Chloroform-d) δ=8.41 (d, J=5.6 Hz, 1H), 7.70 (s, 1H), 7.58-7.51 (m, 2H), 7.36-7.29 (m, 2H), 7.21 (d, J=7.9 Hz, 1H), 6.96 (d, J=5.6 Hz, 1H), 6.87 (dd, J=7.9, 2.4 Hz, 1H), 6.83 (dd, J=7.8, 7.7 Hz, 11H), 6.73 (dd, J=7.9, 2.5 Hz, 1H), 6.07 (s, 1H), 3.83 (s, 3H), 2.44 (s, 3H); $^{13}$C NMR (100 MHz, Chloroform-d) δ=160.8, 158.6, 148.9, 146.5, 145.6, 140.7, 139.0, 133.7, 130.5, 130.0, 129.1, 127.3, 123.8, 121.7, 120.9, 114.5, 110.1, 108.1, 103.0, 55.5, 21.6; Anal. Calcd. for $C_{21}H_{18}N_2OS$: C, 72.80; H, 5.24; N, 8.09. Found: C, 72.53; H, 5.61; N, 8.19.

BK40197

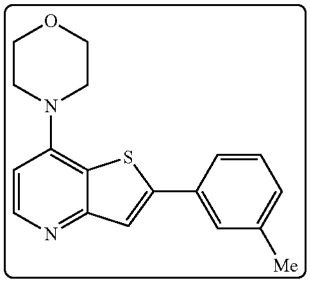

4-(2-(m-Tolyl)thieno[3,2-b]pyridin-7-yl)morpholine (9). Compound 9 was obtained as a colorless solid in 98% yield (91 ng, 0.294 mmol) from 7-chloro-2-(m-tolyl)thieno[3,2-b]pyridine (78 mg, 0.3 mmol) and morpholine (52 mg. 0.6 nmol) in 1 mL of DMSO after 4 days at 100° C. by following the general procedure described above. $R_f$=0.2 (hexanes/EtOAc, 1:1); $^1$H NMR (400 MHz, Chloroform-d) δ=8.48 (d, J=5.4 Hz, 1H), 7.69 (s, 1H), 7.59-7.52 (m, 2H), 7.34 (dd, J=7.9, 7.8 Hz, 1H), 7.20 (dd, J=7.9, 2.1 Hz, 1H), 6.64 (d, J=5.4 Hz, 1H), 4.03-3.85 (m, 4H), 3.54-3.39 (m, 4H), 2.43 (s, 3H); $^{13}$C NMR (100 MHz, Chloroform-d) δ=158.8, 153.0, 149.0, 146.6, 139.0, 133.6, 129.9, 129.1, 127.2, 123.7, 123.4, 121.4, 105.9, 66.9, 49.7, 21.6; Anal. Calcd. for $C_{18}H_{18}N_2OS$: C, 69.65; H, 5.85; N, 9.02. Found: C, 69.89; H, 5.72; N, 9.38.

BK40196

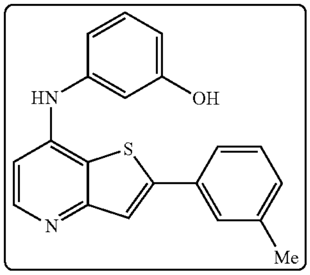

3-((2-(m-Tolyl)thieno[3,2-b]pyridin-7-yl)amino)phenol (10). To a solution of N-(3-methoxyphenyl)-2-(m-tolyl) thieno[3,2-b]pyridin-7-amine (8) (69 mg, 0.2 mmol) in dry dichloromethane (3 mL) was added boron tribromide (4 equiv) at −78° C. under inert atmosphere. The mixture was stirred for 4 h and the reaction temperature was allowed to reach 0° C. After quenching with 1M HCl, the crude reaction mixture was extracted with EtOAc and washed with water. The combined organic layers were dried over sodium sulfate and the solvent was removed in vacuo. The crude product was purified by flash chromatography on silica gel using DCM-MeOH (19:1) as mobile phase. Compound 10 was obtained as a colorless solid in 97% yield (64 mg, 0.194 mmol). $R_1$=0.4 (DCM MeOH, 9:1); $^1H$ NMR (399 MHz, Methanol-$d_4$) δ=8.22 (d, J=6.7 Hz, 1H), 7.70 (s, 1H), 7.65 (s, 1H), 7.61 (dd, J=7.5, 2.1 Hz, 1H), 7.40 (dd, J=7.6, 7.6 Hz, 1H), 7.34-7.31 (m, 2H), 6.93 (d, J=6.7 Hz, 1H), 6.88 (m, 1H), 6.85-6.79 (m, 2H), 2.44 (s, 3H); $^{13}C$ NMR (100 MHz. Methanol-$d_4$) δ=160.1, 154.7, 153.5, 149.5, 141.1, 140.7, 139.5, 133.3, 132.4, 131.9, 131.7, 130.5, 128.2, 125.0, 117.4, 115.7, 114.9, 113.5, 102.7, 21.3; Anal. Calcd. for $C_{20}H_{16}N_2OS$: C, 72.26; H, 4.85; N, 8.43. Found: C, 72.29; H, 4.97; N, 8.61.

Mice

Tauopathy rTG4510 mice (i.e., a mouse model that clinically manifest a tauopathy), expressing human P301L tau driven by a CAMκII promoter, approximately 9-12 months old, were treated intraperitoneally (I.P.) for 21 consecutive days, with 2.5 mg/kg (n=6) BK40197, 5.0 mg/kg (n=6) BK40197, or Dimethyl sulfoxide (DMSO) (n=7).

Behavior

Overnight nest shredding behavior was qualitatively measured on a 0 to 5 scale, with 0 indicating unshredded bedding material and 5 denoting a completely shredded nest that displayed a rounded appearance. Then, blinded, independent observers reviewed images of the overnight shredding and the average quality scores were calculated.

Open-field behavior was assessed in an open-field apparatus where animals were tracked by photocell beams along the arena floor for 60 minutes. Data were collected and analyzed for total distance traveled (cm), total time spent moving (sec), and velocity (distance/time) during the 60-minute trial. A center zone was digitally defined in the software, in the center of the apparatus, and center zone entries during the 60-minute trial were recorded.

Western Blot

Samples collected from DMSO, 2.5 mg/kg-, and 5.0 mg/kg-treated animals were electrophoresed in a NuPAGE 10% Bis-Tris gel and transferred to a nitrocellulose membrane. Membranes were then probed for total human tau (HT-7 antibody and Tau-5 antibody) and phospho-tau (pTau AT180 antibody and pTau AT8 antibody), as well as actin, and treated with an anti-mouse secondary antibody, before exposure using SuperSignal West Dura (Thermo Fisher Scientific, Waltham, MA) substrates. Some animals were excluded from analysis due to low transgene expression.

ELISA pTau Ser396 (Invitrogen, Cat. No. KHB7031, Carlsbad, CA) were performed according to manufacturer's protocol on samples collected from DMSO, 2.5 mg/kg-, and 5.0 mg/kg-treated animals. Samples for ELISA were total brain lysates extracted in 1×STEN buffer.

Statistical Tests

For nest shredding, Mann-Whitney analysis was used within groups, between timepoints, and Kruskal-Wallis analysis was used between treatment groups. For open-field studies: ordinary one-way ANOVA or Student's t test was used.

Results

Figure 5A:
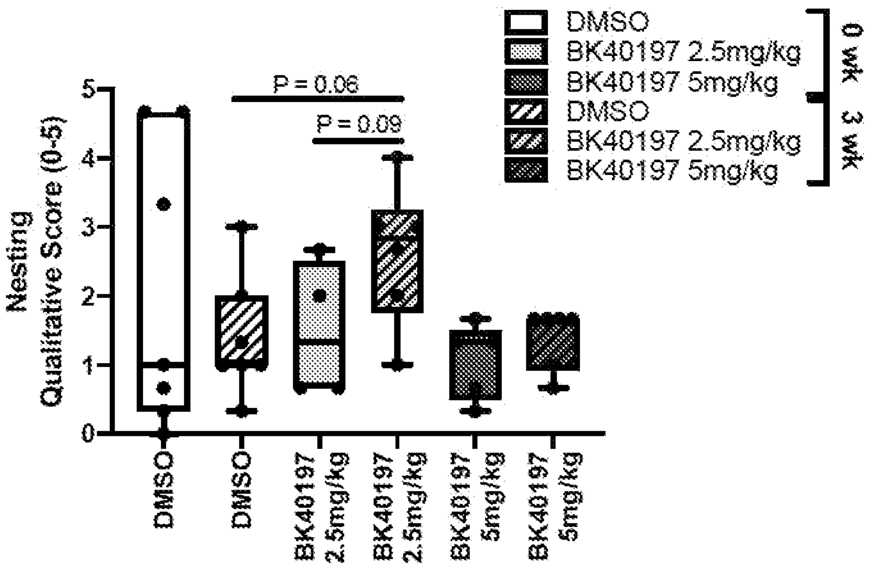
FIG. 5A shows that BK40197 improves nesting behavior in tauopathy rTG4510 mice expressing human P301L tau driven by a CAMκII promoter. Nesting raw scores show an increase in performance in animals treated with 2.5 mg/kg BK40197 for three weeks, as compared to 0 weeks (Mann-Whitney P=0.09), and as compared to animals treated with DMSO for three weeks (Kruskal-Wallis P=0.06).
Figure 5B:
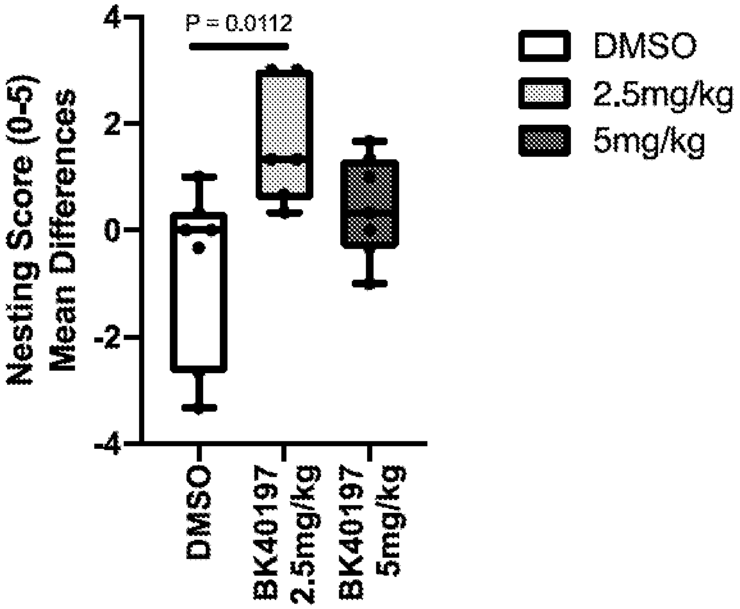
FIG. 5B shows that BK40197 improves nesting behavior in tauopathy rTG4510 mice expressing human P301L tau driven by a CAMκII promoter. Nesting mean difference scores for treatment groups show an increase in performance in animals treated with 2.5 mg/kg BK40197 for three weeks, as compared to animals treated with DMSO for three weeks (Knuskal-Wallis P=0.06).

Shredding and nesting are commonly used in these mice as a model to for test for ADHD and autism spectrum disorders. BK40197 improved nesting behavior abnormalities in TG4510 transgenic mice. As shown in FIGS. 5A and 5B, after three weeks of treatment, nesting performance improved, as measured by a nesting qualitative score and nesting score mean differences, respectively, in mice treated with 2.5 mg/kg BK40197, as compared to mice treated with DMSO.

Figure 6A:
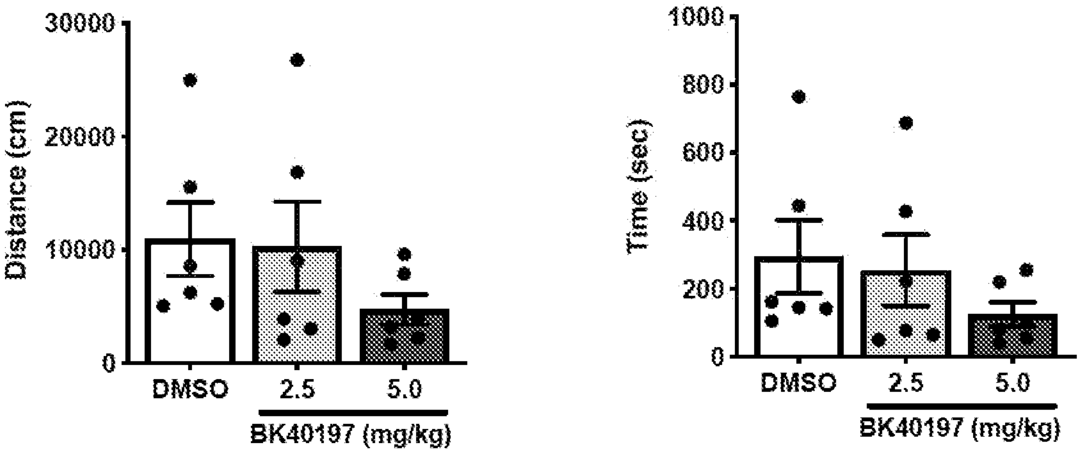
FIG. 6A shows that treatment with 5.0 mg/kg BK40197 does not alter overall motor ability in rTG4510 mice. Open-field measurements, over sixty minutes, show a non-significant reduction in distance (ordinary, one-way ANOVA p-value=0.29; unpaired, one-tailed Welch's t-test p-value=0.61) and time (ordinary, one-way ANOVA p-value=0.32; impaired, one-tailed Welch's t-test p-value=0.09) for mice treated with 5.0 mg/kg BK40197, as compared to animals treated with DMSO, for distance (left panel) (ordinary, one-way ANOVA p-value=0.29; unpaired, one-tailed Welch's t-test p-value=0.61) and time (right panel) (ordinary, one-way ANOVA p-value=0.32; unpaired, one-tailed Welch's t-test p-value=0.09).
Figure 6B:
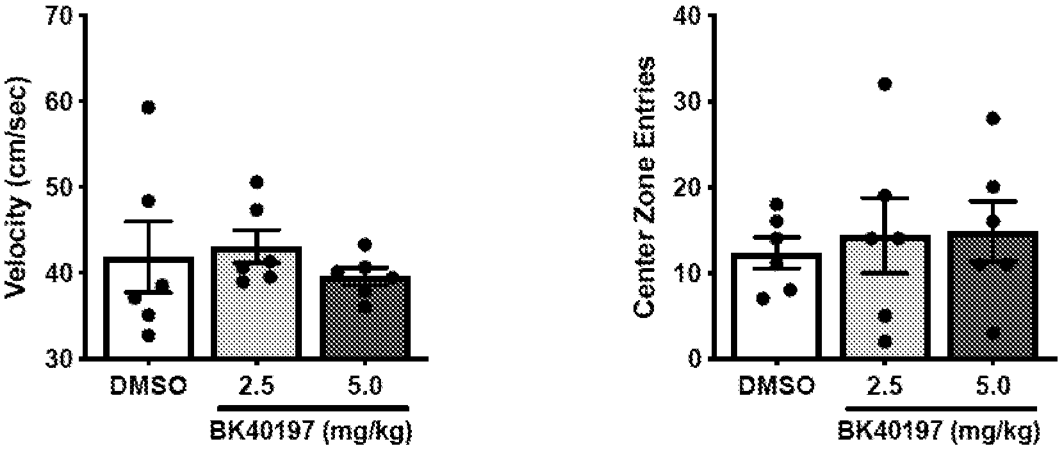
FIG. 6B shows that there is no difference in velocity (left panel) and no sign of hyperactivity % anxiety in rTG4510 mice treated with 5.0 mg/kg BK40197, as compared to mice treated with DMSO, as measured by observed center zone entries (right panel).

Open-field studies shows that BK40197 does not alter overall motor ability in TG4510 transgenic mice. As shown in FIG. 6A (left panel), after treatment with 5.0 mg/kg BK40197, there was a non-significant reduction in distance travelled, as compared to treatment with DMSO. There was also a non-significant reduction in time spent moving (FIG. 6A, right panel). This decrease in distance and time did not reflect an overall change in motor ability of the mice, as determined by the velocity of the mouse's movements (FIG. 6B, left panel). There was no difference in velocity between any treatment groups and no sign of hyperactivity/anxiety by observed center zone entries (FIG. 6B, right panel).

Figure 7A:
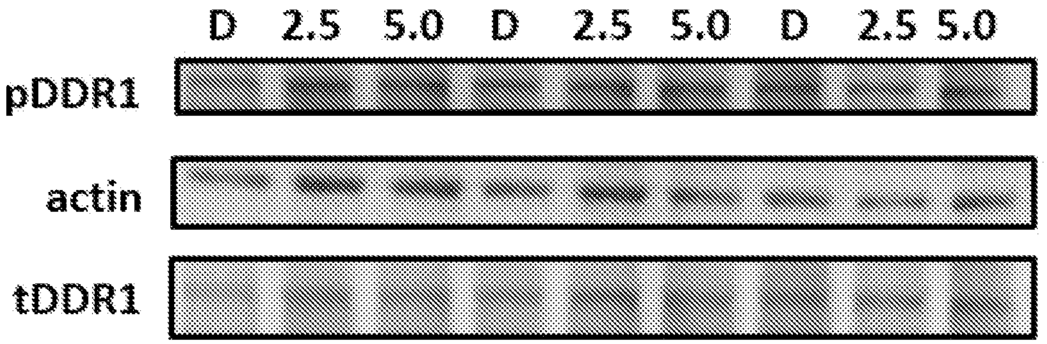
FIG. 7A is a Western blot showing that administration of 2.5 mg/kg BK40197 resulted in a 22% reduction in phosphorylated DDR1 (pDDR1 Tyr513,296), as compared to DMSO and normalized to actin. Ordinary, one-way ANOVA (p-value=0.2), one-tailed t-test (p-value=0.1). Administration of 5.0 mg/kg BK40197 resulted in a 21% reduction in pDDR1 Tyr513,296 compared to DMSO normalized to actin. Ordinary, one-way ANOVA (p-value=0.3), one-tailed t-test (p-value=0.1).
Figure 7B:
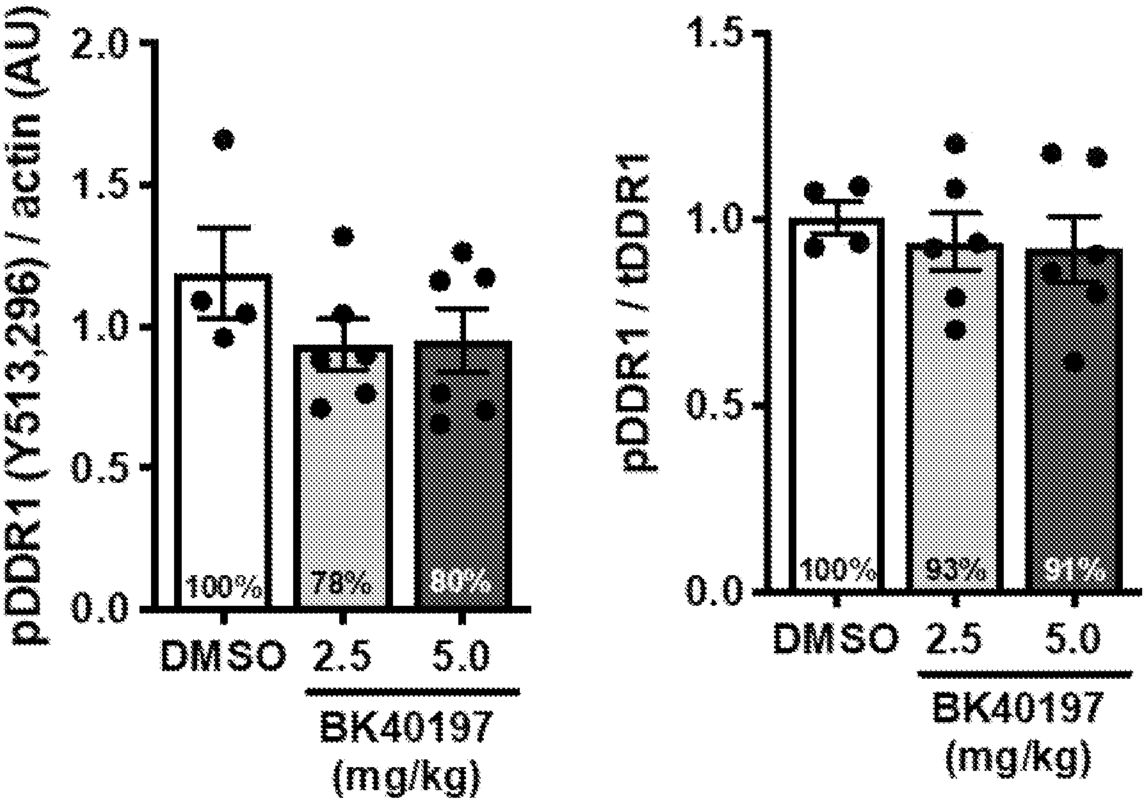
FIG. 7B is a graph showing that administration of 2.5 mg/kg BK40197 resulted in a 22% reduction in pDDR1 Tyr513,296, as compared to DMSO, and normalized to actin (left panel). Ordinary, one-way ANOVA (p-value=0.2), one-tailed t-test (p-value=0.1). Administration of 5.0 mg/kg BK40197 resulted in a 21% reduction in pDDR1 Tyr513, 296, compared to DMSO normalized to actin (right panel). Ordinary, one-way ANOVA (p-value=0.3), one-tailed t-test (p-value=0.1).

Western blot analysis showed that treatment with 2.5 mg/kg BK40197 resulted in a 22% reduction in phosphorylated DDR1 (pDDR1 Tyr513, 296), as compared to treatment with DMSO, when normalized to actin (FIG. 7A). Treatment with and 5.0 mg/kg BK40197 resulted in a 21% reduction in phosphorylated DDR1 (pDDR1 Tyr513, 296), as compared to treatment with DMSO, when normalized to actin (FIG. 7A). FIG. 7B shows the reduction in pDDR1 and the ratio of pDDR1 to total DDR1 (tDDR1) after treatment with 2.5 mg/kg BK40197 or 5.0 mg/kg BK40197.

Figure 8:
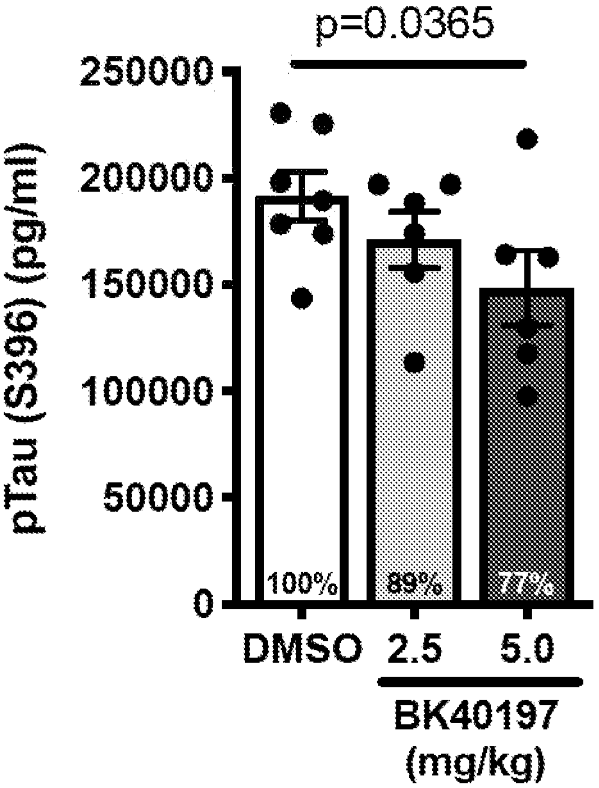
FIG. 8 is a graph showing that administration of BK40197 significantly reduces p-Tau (Ser396) levels in a dose dependent manner, as measured by quantitative EUSA. Administration of 2.5 mg/kg BK40197 resulted in a 11% reduction in pTau S296, as compared to administration of DMSO. Ordinary, one-way ANOVA (p-value=0.49), one-tailed t-test with Welch's correction (p-value=0.13). Administration of 5.0 mg/kg BK40197 resulted in a 23% reduction in pTau S296, as compared to administration of DMSO. Ordinary, one-way ANOVA (p-value=0.07), one-tailed t-test with Welch's correction (p-value=0.03). These mice also showed better nesting and shredding behavior.

As shown in FIG. 8, BK40197 significantly reduces p-Tau (Ser396) levels in a dose dependent manner, as measured by ELISA. These are the same mice that showed better nesting and shredding behavior. Treatment with 2.5 mg/kg BK40197 resulted in an 11% reduction in pTau S296, as compared to treatment with DMSO. Treatment with 5.0 mg/kg BK40197 resulted in a 23% reduction in pTau S296, as compared to treatment with DMSO.

Figure 9A:
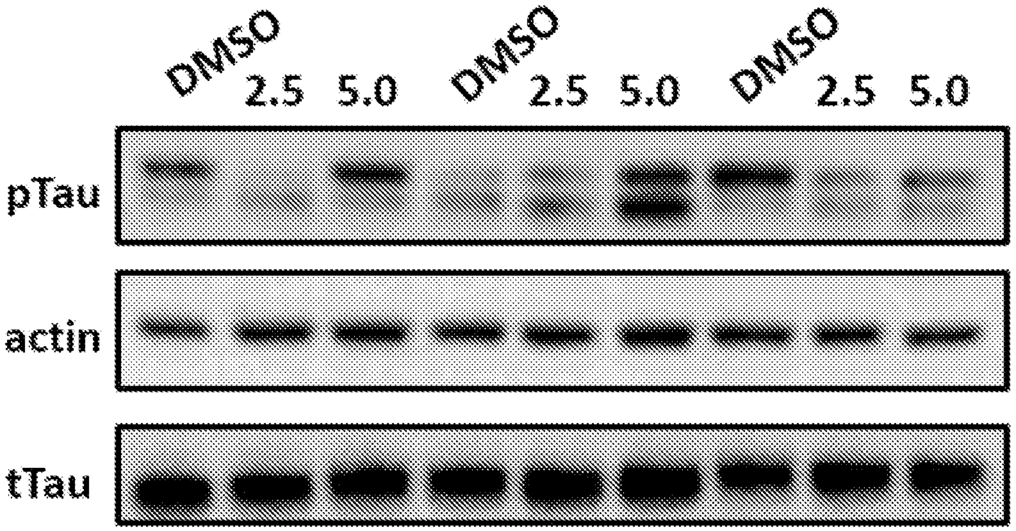
FIG. 9A is a Western blot showing that administration of 2.5 mg/kg BK40197, to rTG4510 mice, reduced p-Tau (Thr231) by more than 20%.
Figure 9B:
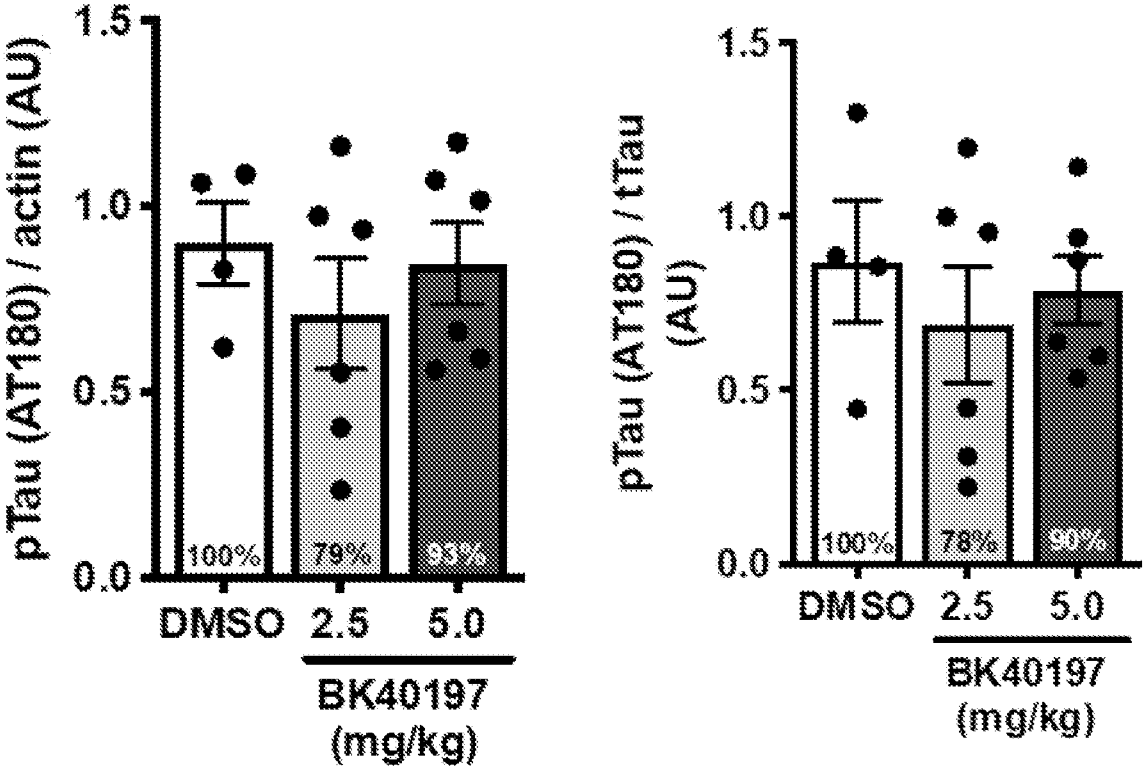
FIG. 9B shows that administration of 2.5 mg/kg BK40197 to rTG4510 mice resulted in a 21% reduction in p-Tau (Thr231) (AT180), as compared to administration of DMSO (left panel). Ordinary, one-way ANOVA (p-value=0.5), one-tailed t-test (p-value=0.16) n=5-6. Also shown is that administration of 2.5 mg/kg BK40197 to rTG4510 mice resulted in a 22% reduction in the ration of p-Tau (Thr231) (AT180) to total Tau (tTau), as compared to administration of DMSO (left panel).

A semi-quantitative Western blot showed that treatment with 2.5 mg/kg BK40197 reduced p-Tau AT180 (Thr231) by more than 20% in TG4510 mice (FIG. 9A). FIG. 9B shows that treatment with 2.5 mg/kg BK40197 reduced the ratio of p-Tau Thr231 (AT180) to total Tau, by 22%, as compared to treatment with DMSO.

Figure 10A:
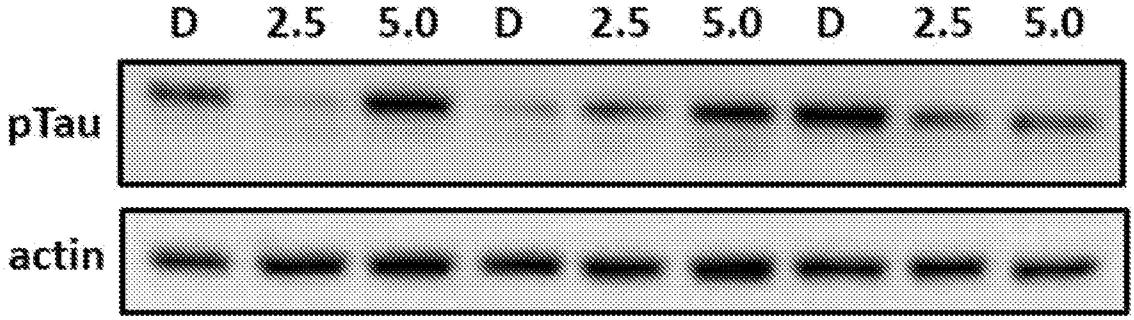
FIG. 10A is a Western blot showing that administration of 2.5 mg/kg BK40197 to rTG4510 mice reduced p-Tau AT8 (Ser202, Thr205) by more than 20%.
Figure 10B:
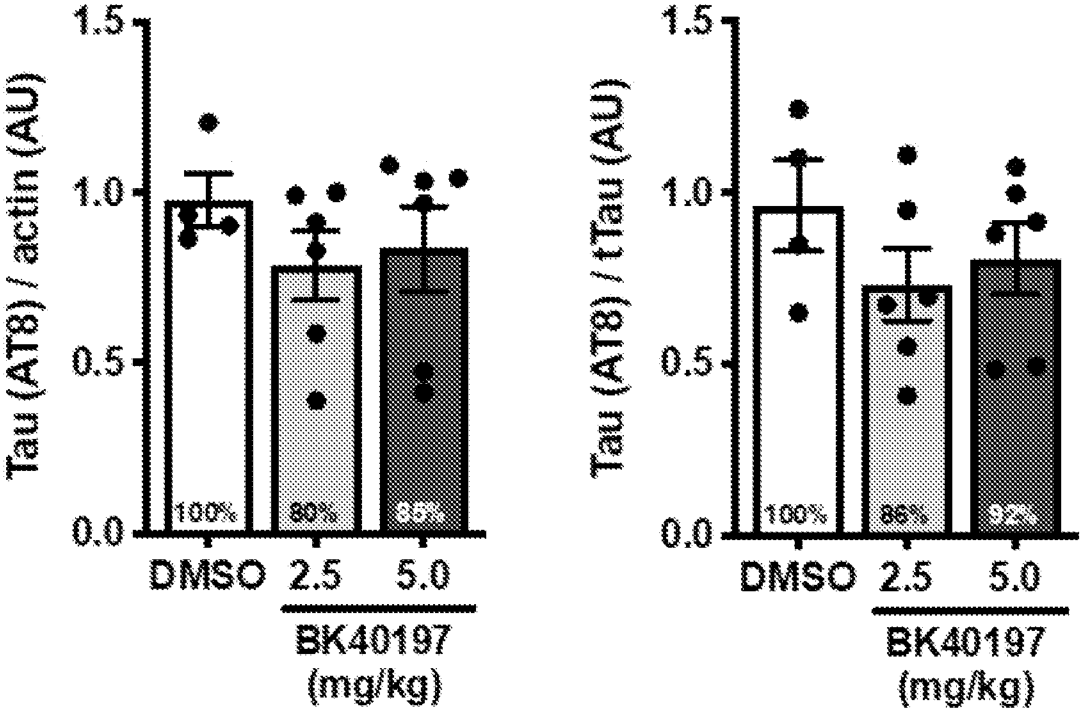
FIG. 10B shows that administration of 2.5 mg/kg BK40197 to rTG4510 mice resulted in a 20% reduction in p-Tau AT8 (Ser202, Thr205), as compared to administration of DMSO (left panel). Ordinary, one-way ANOVA (p-value=0.5), one-tailed t-test (p-value=0.16) n=5-6. Also shown is that administration of 2.5 mg/kg BK40197, to rTG4510 mice, resulted in a 14% reduction in the ration of p-Tau AT8 (Ser202, Thr205) to total Tau (tTau), as compared to administration of DMSO (left panel).

Western blot analysis also showed that treatment with 2.5 mg/kg BK40197 reduced p-Tau AT8 (Ser202. Thr205) by 20% in TG4510 mice (FIG. 10A). FIG. 10B shows that treatment with 2.5 mg/kg BK40197 reduced the ratio of Tau AT8 (Ser202, Thr205) to total Tau, by 14%, as compared to treatment with DMSO.

Example 3

In Vivo Experiments for BK5018, BK5029 and CL2-296

Six to twelve old synucleinopathy A53T mice expressing human A53T SNCA were used. 12 month old mice were treated I.P. for 21 consecutive days with 2.5 mg/kg (BK5018 n=3; BK50129 n=5; CL2-296 n=5), 5.0 mg/kg (BK5018 n=0; BK5029 n=4; CL2-296 n=5), 10 mg/kg CL-287-1 (BK5018 n=3; BK5029 n=3; CL2-296 n=3) or dimethyl sulfoxide (DMSO) (n=6). pTau Ser396 (Invitrogen, KHB7031) and alpha-synuclein detection was performed according to manufacturer's protocol on samples collected from DMSO and 2.5 mg/kg, 5.0 mg/kg, and 10 mg/kg treated mice. Samples were total brain lysates extracted in 1×STEN buffer. Ordinary one-way ANOVA or Student's t test was used.

In Vivo Experiments for CL-287-2

Tauopathy rTG4510 mice expressing human P301L Tau driven by CAMκII were treated I.P. for 7 or 21 consecutive days with 1.25 mg/kg, 2.5 mg/kg, 5.0 mg/kg of BK40143 or Dimethyl sulfoxide (DMSO).

pTau Ser396 (Invitrogen, KHB7031) ELISA was performed according to manufacturer's protocol on samples collected from DMSO and 2.5 mg/kg. 5.0 mg/kg, and 10 mg/kg treated mice. Samples were total brain lysates extracted in 1×STEN buffer. Ordinary one-way ANOVA or Student's t test was used. * $P<0.05$ Nesting Behavior Tauopathy rTG4510 mice expressing human P301L tau driven by CAMκII were treated I.P. for 7 or 21 consecutive days with 1.25 mg/kg, 2.5 mg/kg, 5.0 mg/kg BK40143 or Dimethyl sulfoxide (DMSO).

Overnight nest shredding behavior was qualitatively measured on a 0 to 5 scale, with 0 indicating unshredded bedding material and 5 denoting a completely shredded nested that displayed a rounded appearance. Blinded independent observers reviewed images of the overnight shredding and the average quality scores were calculated.

Open-field behavior was assessed in an open-field apparatus where animals were tracked by photocell beams along the arena floor for 60 minutes. Data were collected and analyzed for total distance traveled (cm), total time spent moving (sec), and velocity (distance/time) during the 60-minute trial. A center zone was digitally defined in the software in the center of the apparatus and center zone entries during the 60-minute trial were recorded. Ordinary one, one-way ANOVA or Student's t test was used. $P<0.05$.

Results

Figure 11A:
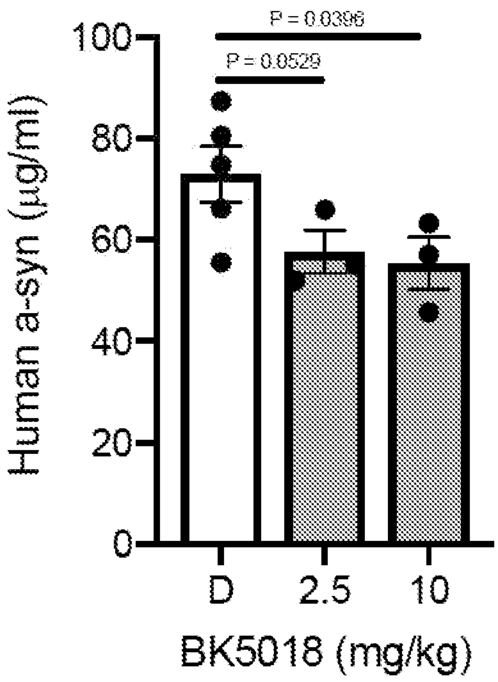
FIG. 11A shows that administration of 2.5 mg/kg and 10 mg/kg BK5018 resulted in a significant reduction of human alpha-synuclein, as measured by ELISA of whole brain lysates from 12 month old A53T mice.
Figure 11B:
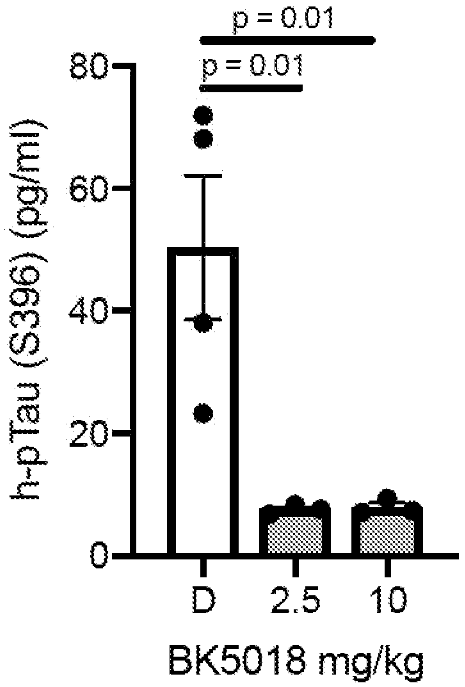
FIG. 11B shows that administration of 2.5 mg/kg and 10 mg/kg BK5018 resulted in a significant reduction of murine Tau, as measured by ELISA of whole brain lysates from 12 month old A53T mice.

As shown in FIG. 11A, administration of 2.5 mg/kg and 10 mg/kg BK5018 resulted in a significant reduction of human alpha-synuclein, as measured by ELISA of whole brain lysates from 12 month old A53T mice. Similarly, a significant reduction in murine Tau was observed (FIG. 11B) showing efficacy of BK5018 for reducing neurotoxic proteins in subjects with Parkinsonism.

Figure 12A:
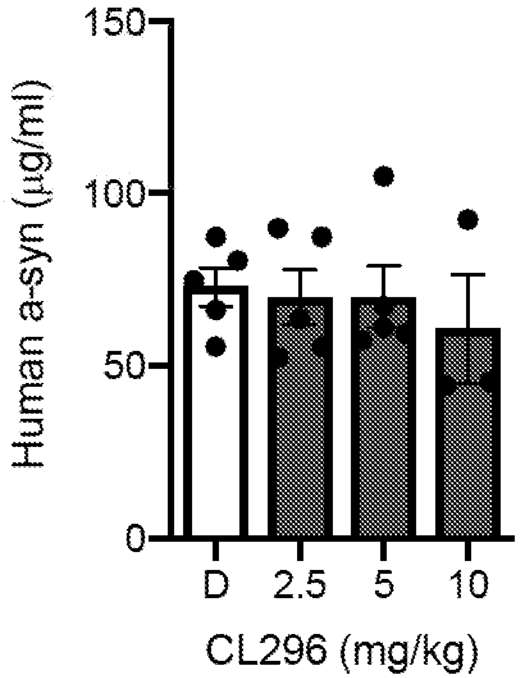
FIG. 12A shows that administration of 10 mg/kg CL2-296 resulted in a trend reduction of human alpha-synuclein, as measured by ELISA of whole brain lysates from 12 month old A53T mice.
Figure 12B:
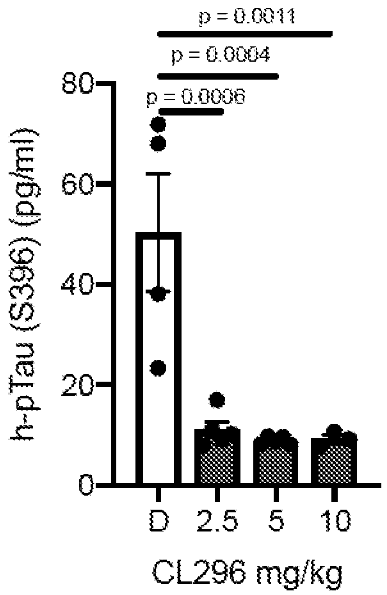
FIG. 12B shows a significant reduction in murine Tau after administration of 2.5 mg/kg, 5 mg/kg and 10 mg/kg CL2-296, as measured by ELISA of whole brain lysates from 12 month old A53T mice.

As shown in FIG. 12A, a trend reduction of human alpha-synuclein was observed after administration of 10 mg/kg CL2-296 (p=0.07), as measured by ELISA of whole brain lysates from 12 month old A53T mice. A significant reduction in murine Tau was observed (FIG. 12B) after administration of 2.5 mg/kg, 5 mg/kg and 10 mg/kg CL2-296, showing efficacy of CL2-296 for reducing neurotoxic proteins in subjects with Parkinsonism.

Figure 13A:
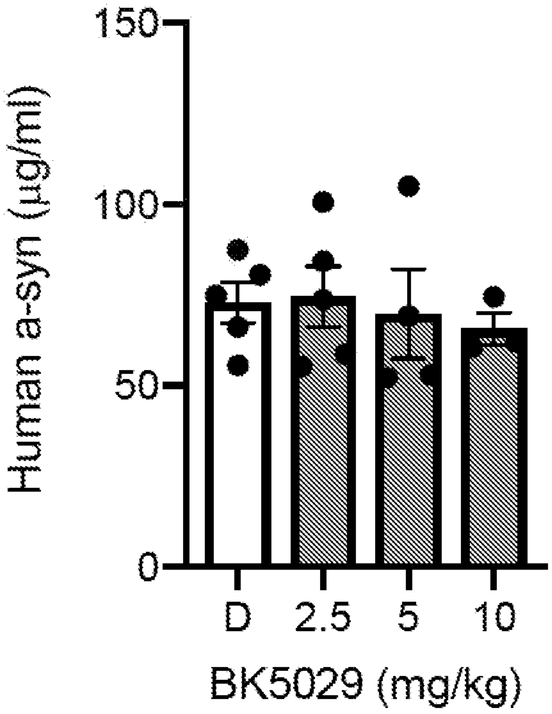
FIG. 13A shows a trend reduction of human alpha-synuclein after administration of 10 mg/kg BK5029 (p=0.07), as measured by ELISA of whole brain lysates from 12 month old A53T mice.
Figure 13B:
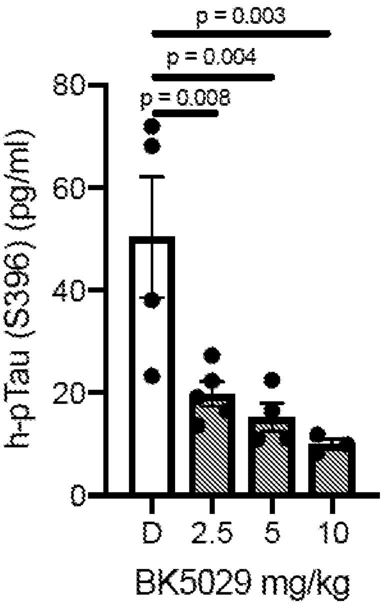
FIG. 13 shows a significant reduction in murine Tau after administration of 2.5 mg/kg, 5 mg/kg and 10 mg/kg BK5029.

As shown in FIG. 13A, a trend reduction of human alpha-synuclein was observed after administration of 10 mg/kg BK5029 (p=0.07), as measured by ELISA of whole brain lysates from 12 month old A53T mice. A significant reduction in murine Tau was observed (FIG. 13B) after administration of 2.5 mg/kg, 5 mg/kg and 10 mg/kg BK5029, showing efficacy of BK5029 for reducing neurotoxic proteins in subjects with Parkinsonism.

Figure 14:
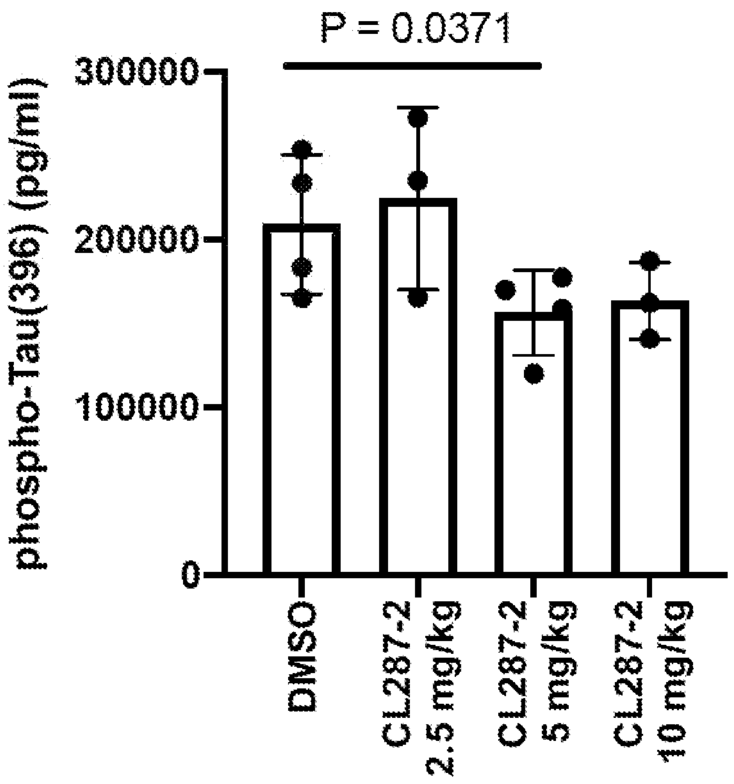
FIG. 14 shows that administration of 5 mg/kg CL-287-2 resulted in significant reduction of tau as measured by ELISA of whole brain lysates from 12 month old rTG4510 mice.

As shown in FIG. 14, administration of 5 mg/kg CL-287-2 resulted in significant reduction of tau as measured by ELISA of whole brain lysates from 12 month old rTG4510 mice. CL-287-2 is effective for reducing neurotoxic hyper-phosphorylated tau in subjects with dementia.

Figure 15:
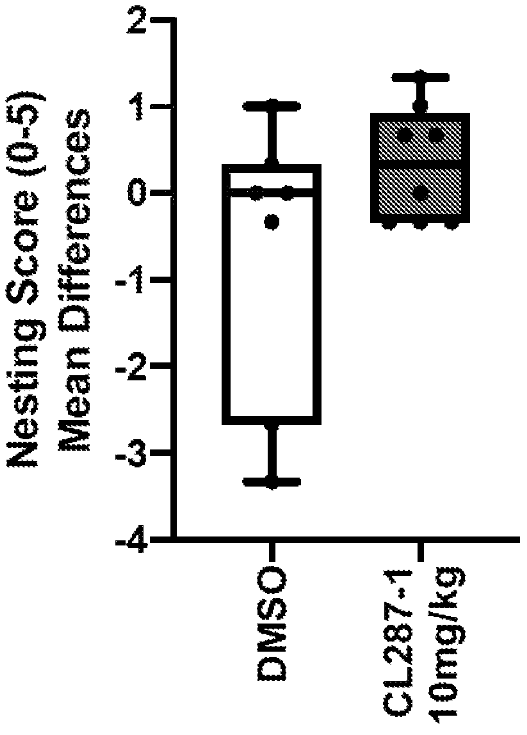
FIG. 15 shows that the nesting mean difference scores over 3 weeks of treatment with 10 mg/kg CL287-1 (Kruskal-Wallis P=0.01) was significantly different, as compared to DMSO, in rTG4510 mice that express mutant P301L Tau and are hyper-active.

As shown in FIG. 15, the nesting mean difference scores over 3 weeks of treatment with 10 mg/kg CL287-1 (Kruskal-Wallis P=0.01) is significantly different, as compared to DMSO, in rTG4510 that express mutant P301L Tau and are hyper-active. CL-287-1 significantly improved nesting behavior in these mice, indicating that the drug positively affects cognition and behavior.

What is claimed is:

1. A compound having the following formula:

Compound 2

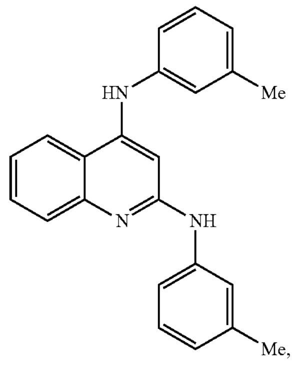

(BK5026)

Compound 3

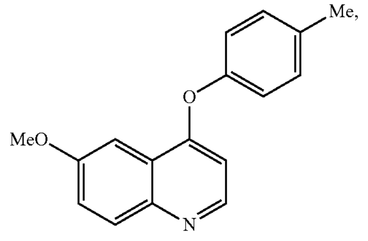

(BK5029)

Compound 4

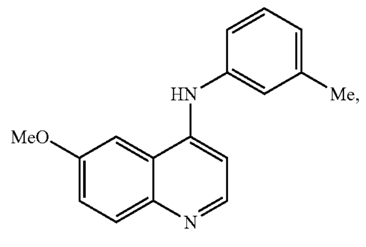

or (BK5030)

-continued

Compound 5

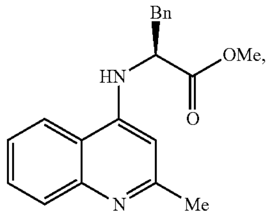

(DH016)

or a pharmaceutically acceptable salt thereof.

2. A method of treating a neurodegenerative disease comprising administering to the subject with the neurodegenerative disease of the central nervous system or at risk for developing the neurodegenerative disease of the central nervous system an effective amount of the compound of claim 1.

3. The method of claim 2, wherein the central nervous system neurodegenerative disease is selected from the group consisting of Amyotrophic Lateral Sclerosis, Alzheimer's Disease, Parkinson's Disease, Huntington's Disease, Mild Cognitive Impairment, an α-Synucleinopathy and a Tauopathy.

4. The method of claim 2, wherein the compound is administered systemically.

5. The method of claim 2, wherein the compound is administered at a dosage of 10 mg/kg or less.

6. The method of claim 2, wherein the compound is in a pharmaceutical composition.

7. The method of claim 2, further comprising administering a second therapeutic agent to the subject.

8. The method of claim 7, wherein the second therapeutic agent is selected from the group consisting of a tyrosine kinase inhibitor, levadopa, a dopamine agonist, an anticholinergic agent, a monoamine oxidase inhibitor, a COMT inhibitor, amantadine, donepezil, memantine, risperidone, rivastigmine, an NMDA antagonist, an acetylcholinesterase inhibitor, a cholinesterase inhibitor, riluzole, an anti-psychotic agent, an antidepressant, and tetrabenazine.

9. The method of claim 8, wherein the tyrosine kinase inhibitor is selected from the group consisting of nilotinib, bosutinib, pazopanib and imatinib.

10. The method of claim 2, wherein the central nervous system neurodegenerative disease is amyloidosis.

11. The method of claim 2, wherein the central nervous system neurodegenerative disease is a secondary neurodegenerative disease induced by a stroke.

* * * * *